(12) United States Patent
Turk et al.

(10) Patent No.: US 6,833,491 B2
(45) Date of Patent: Dec. 21, 2004

(54) MODIFICATION OF POLYSACCHARIDES

(75) Inventors: Stefanus Cornelis Hendrikus Jozef Turk, Leidschendam (NL); Nathalie Gerrits, Houten (NL); Josephus Christianus Maria Smeekens, Driebergen (NL); Petrus Jacobus Weisbeek, Den Dolder (NL)

(73) Assignee: D. J. van der Have B.V., Kapelle (NL)

( * ) Notice: Subject to any disclaimer, the term of this patent is extended or adjusted under 35 U.S.C. 154(b) by 177 days.

(21) Appl. No.: 10/112,797

(22) Filed: Mar. 29, 2002

(65) Prior Publication Data
US 2002/0170092 A1 Nov. 14, 2002

Related U.S. Application Data

(63) Continuation of application No. 09/117,232, filed as application No. PCT/NL97/00039 on Feb. 7, 1997, now abandoned.

(30) Foreign Application Priority Data

Feb. 7, 1996 (NL) .............................................. 1002275

(51) Int. Cl.$^7$ ....................... C12N 15/82; C12N 15/54; C12N 15/62; A01H 5/00; C12P 19/04
(52) U.S. Cl. ....................... 800/284; 800/278; 800/288; 435/69.8; 435/101; 435/193; 435/468
(58) Field of Search ................................. 800/278, 284, 800/288; 435/69.8, 101, 193, 468

(56) References Cited

U.S. PATENT DOCUMENTS 6,087,559 A 7/2000 Nichols ...................... 800/284

FOREIGN PATENT DOCUMENTS

| AU | B-27878/95 | 1/1996 |
|---|---|---|
| CA | 2142308 A1 | 3/1994 |
| CA | 2171313 A1 | 3/1995 |
| DE | 42 27 061 A1 | 2/1994 |
| DE | 43 30 960 A1 | 3/1995 |
| DE | 44 20 223 C1 | 5/1995 |
| WO | WO 89/12386 A1 | 12/1989 |
| WO | WO 94/04692 * | 3/1994 |
| WO | WO 94/14970 A1 | 7/1994 |
| WO | WO 95/13389 A1 | 5/1995 |
| WO | WO 96/01904 A1 | 1/1996 |

OTHER PUBLICATIONS

Smeekens et al. Plant Molecular Biology 9(4): 377–388 (1987).*
Nakano, Y. J., and H. K. Kuramitsu, "Mechanism of *Streptoccus mutans* Glucosyltransferases: Hybrid–Enzyme Analysis," *J. of Bacteriology* 174(17):5639–5646, Sep. 1992.
Van der Meer, I.M., et al., "Fructan as a New Carbohydrate Sink in Transgenic Potato Plants," *The Plant Cell* 6:561–570, Apr. 1994.
Yamamoto, S., et al., "The Mode of Synthesis of Levan by *Bacillus subtilis* Levansucrase," *Agricultural and Biological Chemistry* 49(2):343–349, Jun. 1984.
Fuchs, A., Current and Potential Food and Non–Food Applications of Fructans, *Biochem. Soc. Trans.* 19:555–560, 1991.
Pilon, M., et al., Functional Domains of the Ferredoxin Transit Sequence Involved in Chloroplast Import, *J. Biological Chemistry* 270(8):3882–3893, 1995.
Smeekens, S., et al., "The Plant Ferredoxin Precursor: Nucleotide Sequence of a Full Length cDNA Clone, " *Nucleic Acids Research* 13(9):3179–3194, 1985.
Turk, S., et al., "The Vacuolar Sorting Domain of Sporamin Transports GUS, but not Levansucrase, to the Plant Vacuole," *New Phytol.* 136:29–38, 1997.

* cited by examiner

*Primary Examiner*—David T. Fox
(74) *Attorney, Agent, or Firm*—Christensen O'Connor Johnson Kindness PLLC

(57) ABSTRACT

The present invention relates to a method for manufacturing modified polysaccharide in contact with a sugar group transferring enzyme and a sugar group donor. The result of the method is modified polysaccharides, which can be used for different food and non-food applications.

10 Claims, 13 Drawing Sheets

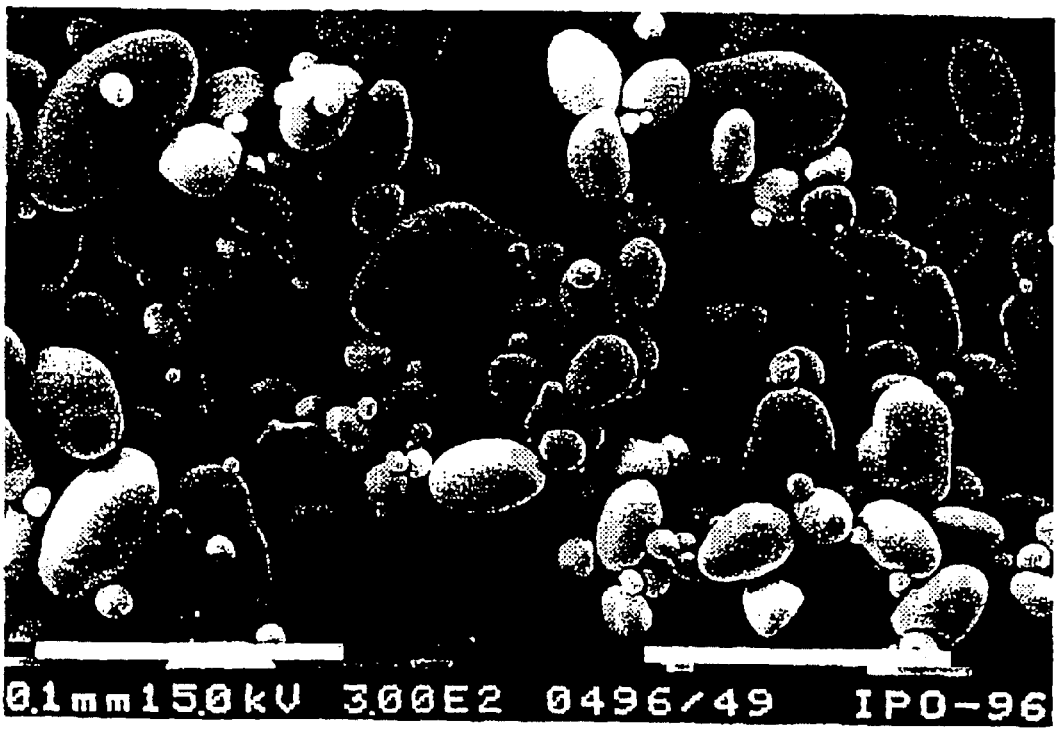
FIG. 6a "Wild type"
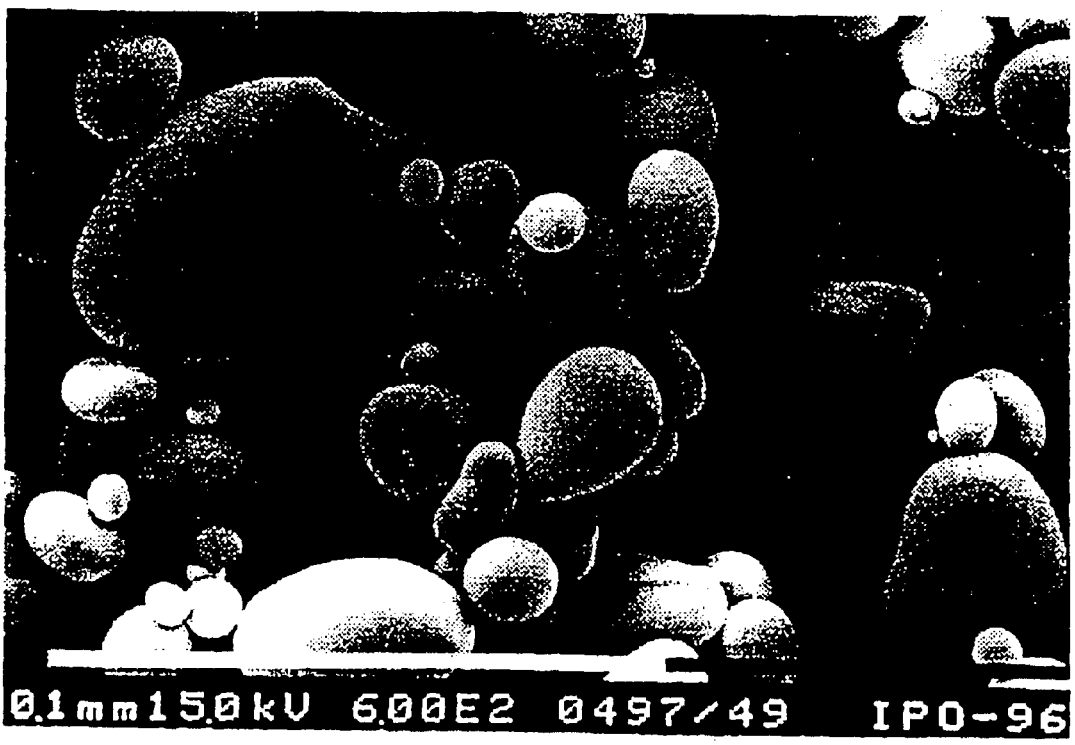
FIG. 6b "Wild type"

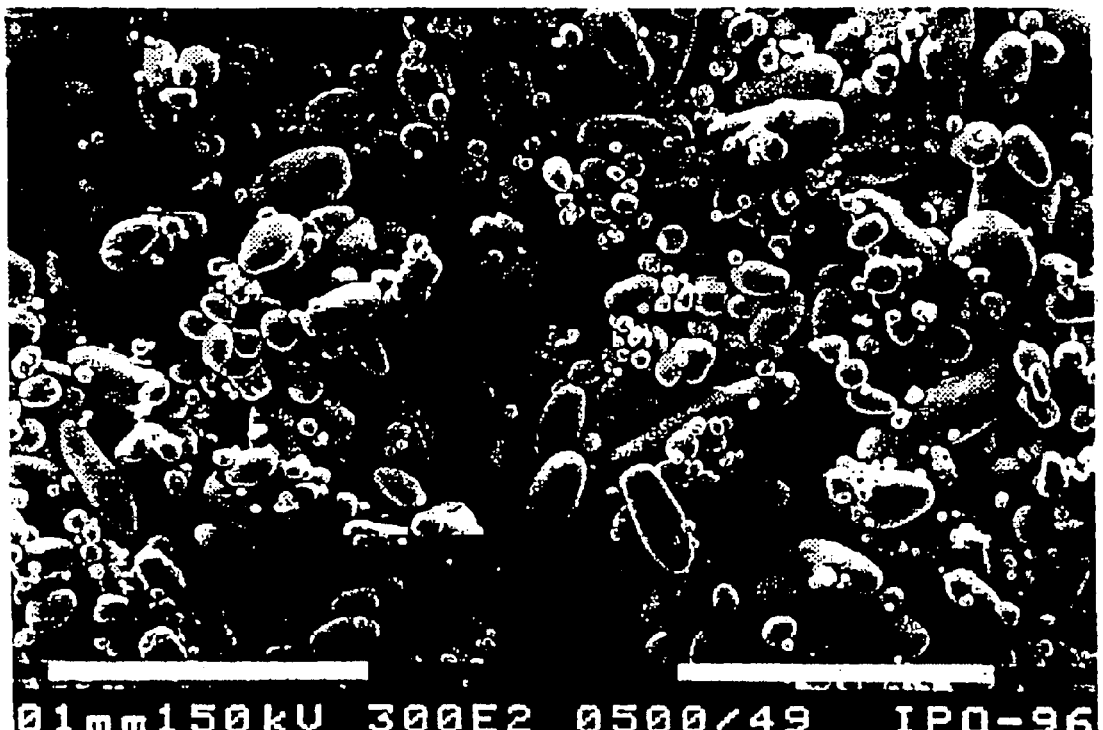
FIG. 6c "192-3"
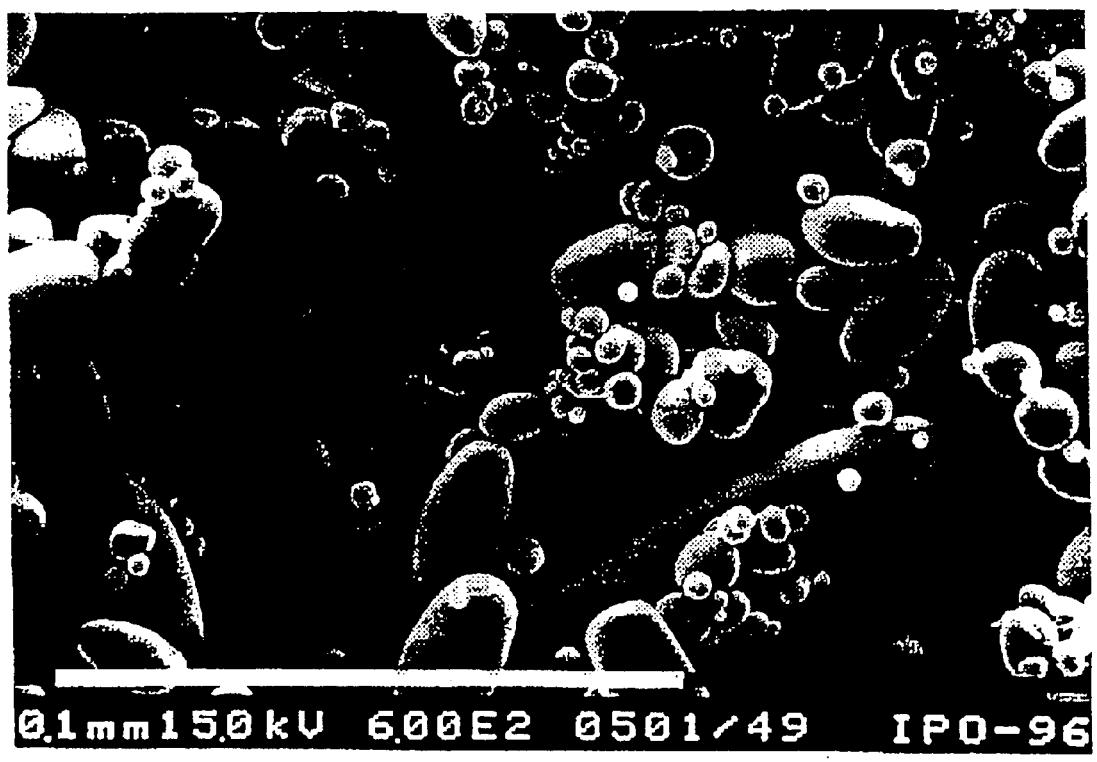
FIG. 6d "192-3"

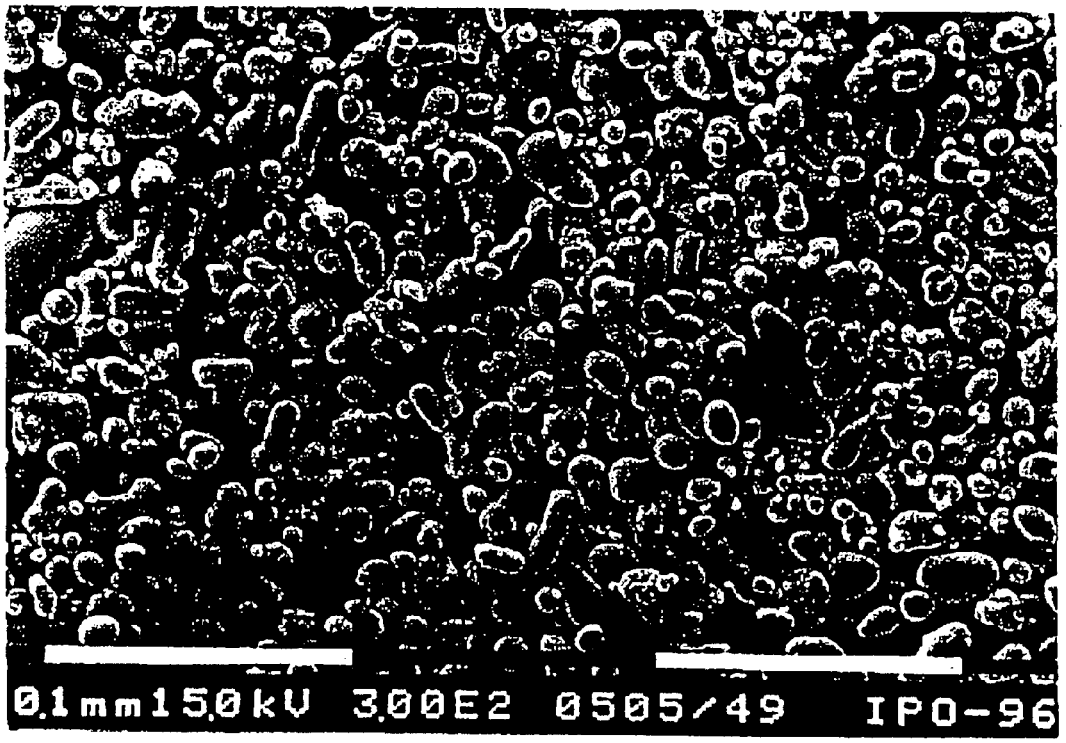
FIG. 6e "192-2"
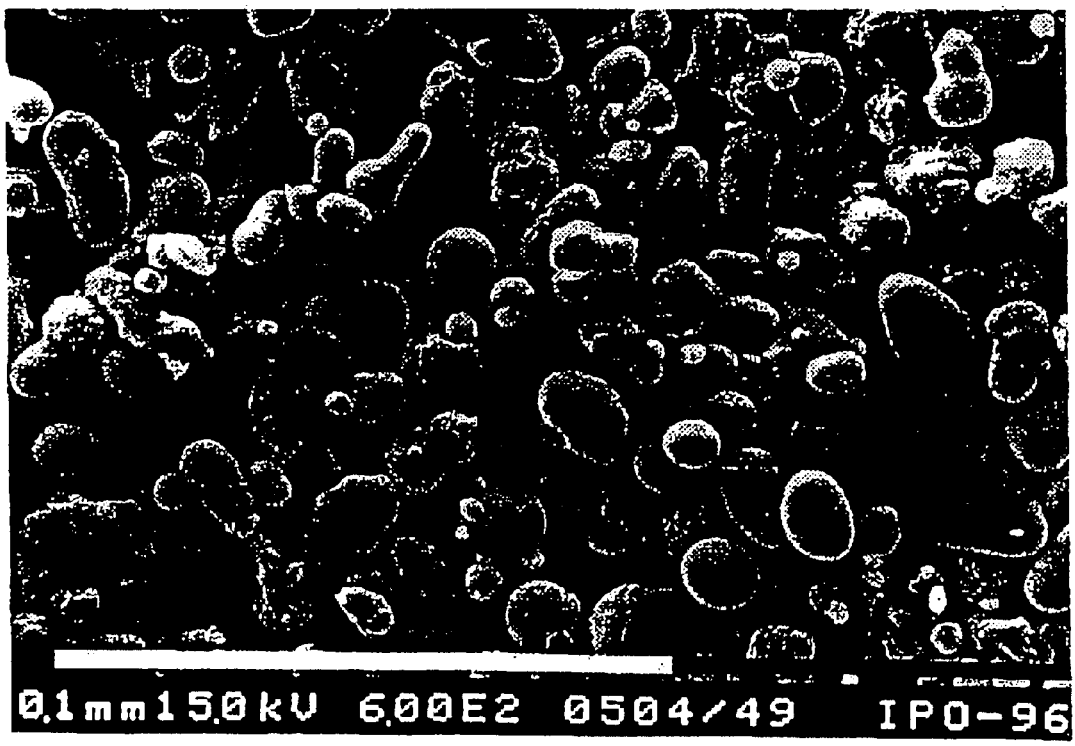
FIG. 6f "192-2"

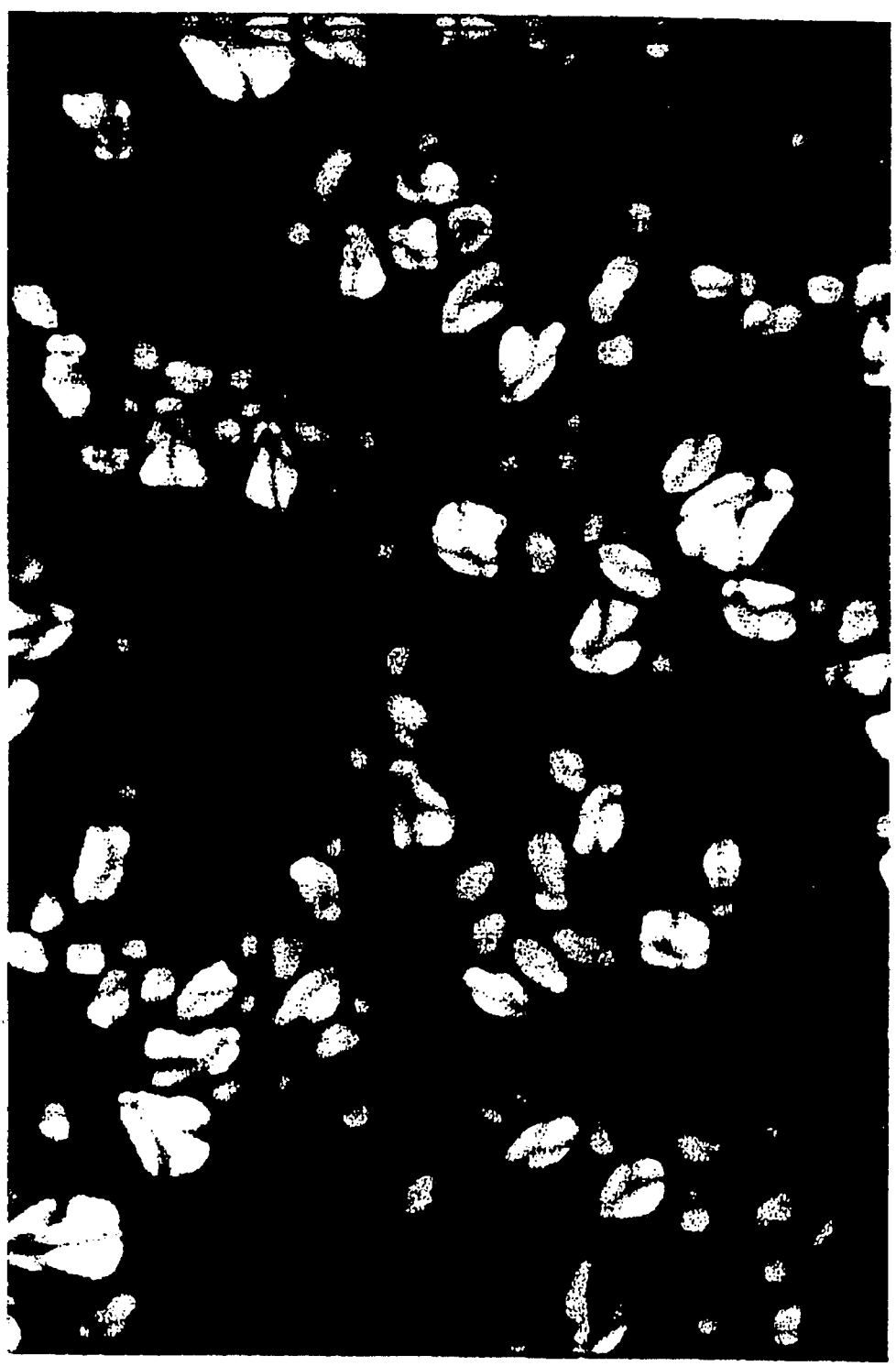
FIG. 7a "Wild type"

FIG. 7b "192-3"

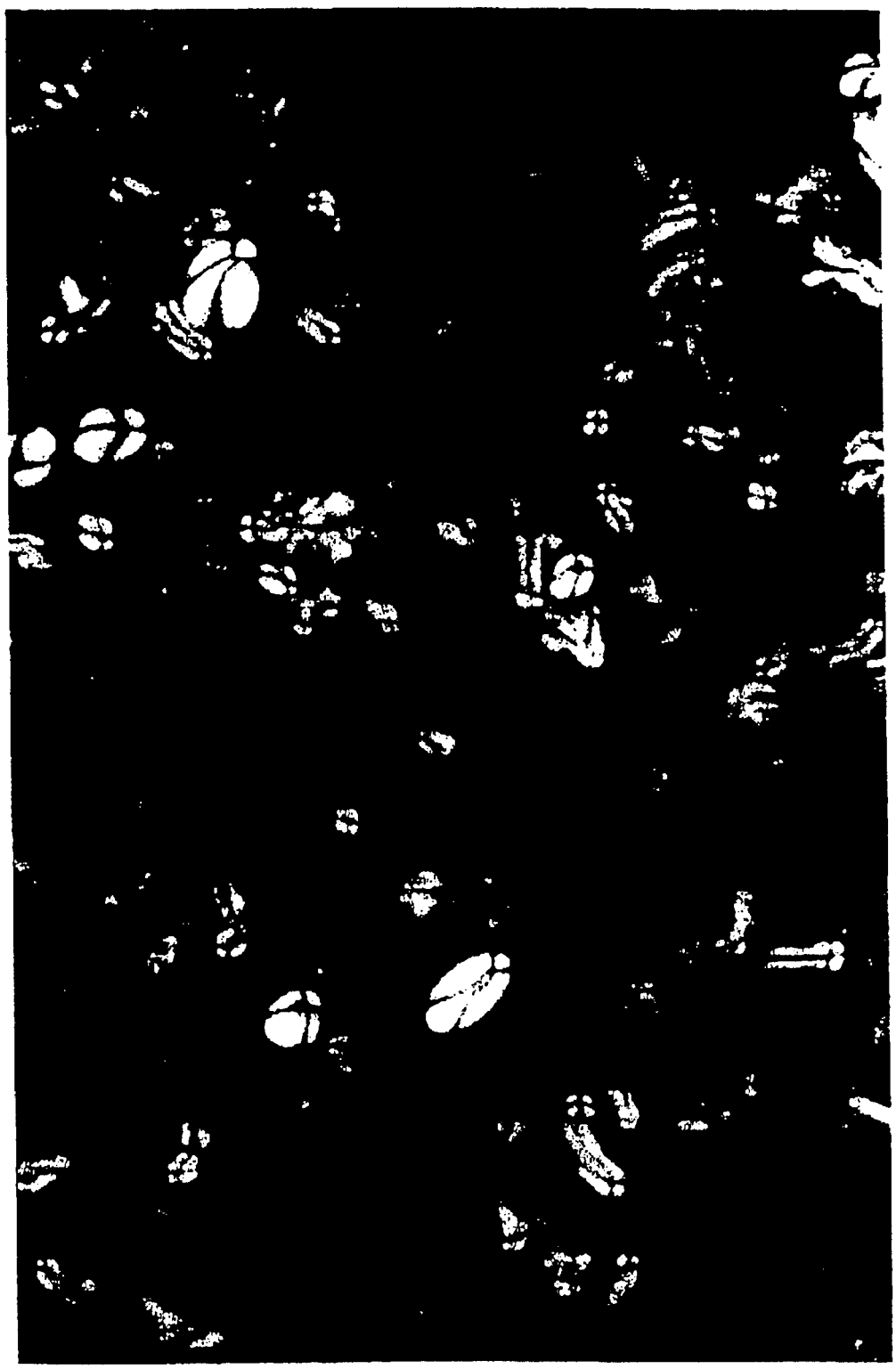
FIG. 7c "192-2"

MODIFICATION OF POLYSACCHARIDES

CROSS-REFERENCES TO RELATED APPLICATIONS

This application is a continuation of prior application Ser. No. 09/117,232, filed Mar. 1, 1999, now abandoned, which is the U.S. national phase of International Application No. PCT/NL97/00039, filed Feb. 7, 1997, which claims priority of Netherlands Application No. 1002275, filed Feb. 7, 1996, priority from the filing dates of which is hereby claimed under 35 U.S.C. §§ 119 and 120.

The present invention relates to the modification of polysaccharides.

BACKGROUND OF THE INVENTION

Polysaccharides, such as starch, cellulose, pectin, hemicellulose and the like have a diversity of applications. Starch for instance has long formed part of the diet of humans and many animals. In addition to food applications, different non-food applications have been developed for starch and also for many other polysaccharides. The industrial use of starch in particular has increased enormously in recent years. Cellulose in turn is for instance used in the production of paper, in textiles, building materials etc.

The polysaccharides occurring in nature have specific properties which are sometimes less suitable for particular applications. In order to provide a polysaccharide with the desired properties for a particular application use is often made of chemical modification. Chemical modification has the drawback that it involves one or more additional processing steps. In addition, the chemical processing of products used in foods has a somewhat undesirable ring to the consumer nowadays.

SUMMARY OF THE INVENTION

It is the object of the invention to provide an alternative, natural manner of modifying polysaccharides. In addition, the invention has for its object to provide new polysaccharides for new application possibilities.

This is achieved by the invention with a method comprising of placing the polysaccharide in contact with a sugar group-transferring enzyme and a sugar group donor. In this manner an enzymatic modification takes place, wherein no (undesirable) chemical agents are used.

According to the invention a distinction can be made between direct and indirect modification. Direct modification entails the sugar group, which is transferred from the sugar group donor, being (covalently) linked to the polysaccharide to be modified. Indirect modification means there is no direct linking but that changes are made in the physiological appearance of the polysaccharide by the sugar group-transferring enzyme. As example hereof can be mentioned the inclusion in a starch granule of a second polysaccharide formed by the sugar group-transferring enzyme. In addition, the transfer of a sugar group to a water molecule can also be seen as an indirect modification. In such a transfer to water, sucrose is cleaved into glucose and fructose. Due to such a cleaving the physiological conditions in the plant cell change which can result in a change in the physiological appearance of the polysaccharide, such as for instance in the form and size of a starch granule.

The sugar group-transferring enzyme can be any enzyme which, as the name already indicates, transfers a sugar group from a sugar group donor to an acceptor molecule. Such enzymes are usually referred to as transferases. The acceptor molecule will usually be the polysaccharide to be modified. In the case of indirect modification there is another acceptor, such as sucrose of glucose. In the case of transfer to water, water is the acceptor and the enzyme is usually referred to as invertase. In principle, all transferases have to a greater or lesser extent the capacity to use water as acceptor. These enzymes are called transferases or invertases in accordance with the proportion of transferase or invertase activity. The sugar group for transferring can consist of one or more sugar units. In the case of invertases or invertase activity only one sugar unit is transferred.

The invention relates particularly to the use of fructosyl transferases or glucosyl transferases as sugar group-transferring enzymes and fructosyl donors and glucosyl donors as sugar group donor. In the continuation of the application fructosyl transferases and/or glucosyl transferases in particular will be discussed by way of example. Other sugar group-transferring enzymes can however be applied instead of these without departing from the invention. The transfer of a sugar group to water is also included hereinbelow.

DETAILED DESCRIPTION OF THE INVENTION

Fructosyl transferases (FTFs) are enzymes, which are capable of transferring fructosyl units from a fructosyl donor, for instance sucrose, to an acceptor. Fructans can inter alia be formed in this manner which consist almost wholly of repeating fructose units. The number of units in a fructan molecule can vary from 3 to more than 100,000. The type of mutual binding between the fructose units can be β-2,1 as well as β-2,6 (Suzuki & Chatterton (eds) Science and Technology of fructans, CRC Press Inc., Florida, USA (1993)).

Known fructosyl transferases are for instance levan sucrase, invertase, SST, SFT, GFT (also known now as 6G-FFT), FFT (Steinmetz at al., Mol. Gen. Genet. 200, 220–228 (1985), Angenent et al., pp. 173–184. Inulin and inulin-containing crops, A. Fuchs (Ed), Koops et al., J. Exp. Botany 45, 1623–1631 (1994), Sprenger et al., Proc. Natl. Acad. Sci. USA 92, 11652–11656 (1995)), Koops et al., Plant Physiol. 110, 1167–1175 (1996), Lüscher et al., FEBS Letters 385, 39–42 (1996), Taussig & Carlson, Nucl. Acids Res. 11, 1943–1953 (1983), Arai et al., Plant Cell Physiol. 33, 245–252 (1992), Klann et al., Plant Physiol. 99, 351–353 (1992), Zhou et al., Plant Physiol. 106, 397–398 (1994), Schwebel-Dugué et al., Plant Physiol. 104, 809–810 (1994)).

Glucosyl transferases (GTFs) can likewise use sucrose as sugar group donor (of glucosyl groups). Glucosyl transferases can result inter alia in the formation of dextrans, glucose polymers of a minimum of 2 glucose units, which can be connected α-1,6 or α-1,3. Dextrans have various applications and are used inter alia as bulk agent in plasma-replacing preparations.

Known glucosyl transferases are for instance alternan sucrase, GTF-I, GTF-S and GTF-SI (Cote, Carbo. Polym., 19, 249–252 (1992); Griffard et al., J. Gen. Micro. 139, 1511–1522 (1993)). Different enzymes result in polymers of different length and type of binding.

The fructosyl and glucosyl transferases used according to the invention can be of natural origin, i.e. isolated from a plant or micro-organism. In addition, they can be recombinantly manufactured and optionally genetically modified versions of the natural enzyme. A modified version can for instance be a fructosyl or glucosyl transferase with an increased substrate affinity. Such modified versions can for instance be produced by using gene constructs manufactured with the aid of recombinant DNA techniques and serve for instance to increase the quantity of fructose covalently linked to the polysaccharide.

Placing of the polysaccharide in contact with the enzyme can be effected in vivo as well as in vitro. The starting point in vivo is a transgenic plant cell in which the enzyme is expressed. The modified polysaccharide is produced in the plant and can easily be isolated therefrom, possibly in the same manner as the native polysaccharide would also be isolated.

An in vivo method according to the invention comprises the steps of:
a) manufacturing a gene construct comprising at least one DNA sequence which codes for a sugar group-transferring enzyme, optionally operably linked to a targeting signal sequence, which DNA sequence is further optionally operably linked to transcription initiation signals located upstream and optionally operably linked to transcription termination signals located downstream;
b) transforming a plant cell with the gene construct;
c) multiplying the transformed plant cell; and
d) optionally isolating modified polysaccharides from the plant cell.

If the DNA sequence which codes for a sugar group-transferring enzyme integrates into the plant genome, transcription initiation signals and/or transcription termination signals are not per se necessary. In such a case signals already present in the genome can be used.

Multiplying of the transformed plant cell can take place in different ways. Regeneration to plant tissue such as callus or the like or to a complete plant can thus take place. In addition, plant cells in suspension can also be multiplied. The oligosaccharide is then isolated from the tissue, the plant or the cells in suspension.

The gene construct can further also comprise at least one DNA sequence which codes for a substrate affinity-providing peptide sequence. The enzyme is hereby brought into close contact with the substrate to be modified. This enhances the modification efficiency. The substrate affinity-providing peptide sequence is operably linked to and preferably lies in reading frame with the sequence which codes for the enzyme.

In the case of starch modification the substrate affinity-providing sequence is preferably chosen from the group consisting of the maltose-binding protein of *Escherichia coli*, the granule-bound starch synthase protein, the starch synthase protein, the branching enzyme, the D-enzyme from plants or micro-organisms and/or fragments and/or isoforms thereof (Baba et al., Plant Phys. 103, 565–573 (1993); Boyer & Preiss, Biochem. Biophys. Res. Comm. 80, 169–175 (1978); Denyer et al., Planta 196, 256–265 (1995); Dry et al., Plant J. 2, 193–202 (1992); Kakefuda & Duke, Plant Phys. 91, 136–143 (1989)).

In the case of cellulose modification it is possible for instance to opt for the cellulose-binding domain of the glucoamylase of *Aspergillus*, the scaffoldine of *Clostridium thermocellum* (Tibtech 13, 447–450 (1995)), or of cellulases of fungi (Reinikainen et al., Proteins 14, 475–482 (1992)) These proteins or protein fragments can be linked C-terminally as well as N-terminally to the fructosyl or glucosyl transferase enzyme.

Pectin-binding domains can come from pectinases, while fructanases have fructan-binding domains. Fructan-binding domains are for instance important when glucosyl transferases are used for modifying fructans.

By means of the targeting signal sequence the enzyme is targeted to the location of the substrate in the plant. Such targeting signal sequences can for instance be plastid-specific, cell wall-specific or vacuole-specific. Plastid-specific targeting signals are used in particular for starch modification since starch is situated in chloroplasts and amyloplasts. In contrast, cellulose is a cell wall constituent and modification thereof will take place by directing the enzyme to the cell wall. The same applies for pectin, hemicellulose, mannans, arabinans and xylans. Present in the vacuole are inter alia stachyose, verbascose, ajugose and other members of the raffinose oligosaccharide family (Bachmann & Keller, Plant Phys. 109, 991–998 (1995)). To enable enzymatic modification thereof the enzyme must be directed to the vacuole. When no targeting sequence is present in the gene construct the enzyme is expressed in the cytoplasm.

A plastid-specific targeting signal sequence preferably codes for a peptide from the group consisting of the ferredoxin of *Silene pratensis*, plastocyanin of *Silene pratensis*, ferredoxin of *Arabidopsis thaliana*, plastocyanin of *Arabidopsis thaliana* (Smeekens et al., Nucl. Acids Res. 13, 3179–3194 (1985); Smeekens et al., Nature 317, 456–458 (1985); Vorst et al., Plant Mol. Biol. 14, 491–499 (1990) and Vorst et al., Gene 65, 59–69 (1988)).

An example of cell wall-specific targeting-signals is the apoplastic targeting signal of the pathogenesis-related protein S (PR-S) (Cornelissen et al., Nature 321, 531–532 (1986), and as vacuole-specific signals can for instance be mentioned the targeting signals of the proteins patatin (Sonnewald et al., Planta 179, 171–180 (1989)), sporamin (Matsuoka et al., J. Biol. Chem. 265, 19750–19757 (1990)), chitinase (Neuhaus et al., Proc. Natl. Acad. Sci. USA 88, 10362–10366 (1991)) and lectin (Wilkins et al., Plant Cell 2, 301–313 (1990)).

For expression of the glucosyl or fructosyl transferase (fusion) gene in plant tissue specific expression signals are of course required which are active in plants. These signals can be supplied together with the gene construct but, if the construct integrates into the genome, expression signals already present in the genome can also be used. A well-known generally used promoter for gene expression in plants, which can be included for instance in the gene construct, is the 35S promoter of the cauliflower mosaic virus. This promoter is active in many tissues of the plant, irrespective of the stage of development. In addition, strong or weak, tissue-specific or development-regulated or other types of promoters can be used as desired, depending on the plant species and the purpose. In the case of modification of starch by fructosyl or glucosyl transferases in the tubers of cultivated crops such as potato, a strong tuber-specific promoter is recommended, such as the promoter of the granule-bound starch synthase (Visser et al., Plant Mol. Biol. 17, 691–699 (1991)), the patatin promoter (Sonnewald et al., Planta 179, 171–180 (1989)) or the sporamin promoter of *Ipomoea batatas* (Nakamura et al., Plant Phys. 96, 902–909 (1991)).

In order to enable a further increase in the transcription levels the promoter sequence is often provided with an enhancer duplication.

In the case of starch modification in the seeds of starch-containing crops, such as corn, wheat, pea or rice, a strong seed-specific promoter is recommended which is active in storage tissue, such as the endosperm of corn, wheat and rice and the seed lobes of peas. Examples of such promoters are for instance the seed-specific rita-1 promoter of rice (Izawa et al., Plant cell 6, 1277–1287 (1994)), the endosperm-specific Opaque-2 and zein promoter from corn (Gallusci et al., Mol. Gen. Genetics 244, 391–400 (1994), Kirihara et al., Mol. Gen. Genetics 211, 477–484 (1988), Kirihara et al., Gene 71, 359–370 (1988)). Further the β-phaseolin promoter (Riggs, Plant Sci. 63, 47–57 (1989), Buston et al., EMBO J. 10, 1469–1479 (1991)), the napin promoter (Radke et al., Theor. Appl. Genet. 75, 685–694 (1988), Kohno-Murase et al., Plant Mol. Biol. 26, 1115–1124 (1994)), the β-conglicinin promoter (Lessard et al., Plant Mol. Biol. 16, 379–413 (1991)), the lectin promoter (Okamura et al., Proc. Natl. Acad. Sci. USA 83, 8240–8244 (1986)), the phytohaemagglutinin promoter (Riggs et al., Plant Cell 1, 609–621 (1989)) and the canavalin promoter (Yamamoto et al., Plant Mol. Biol. 27, 729–741 (1995)).

The translation of the mRNAs can be improved by further adding to the construct a translational enhancer, for instance the Alfalfa Mosaic Virus RNA4 translational enhancer signal which must be present in the 5' transcribed but non-translated region.

For a correct termination of the RNA synthesis a termination signal is preferably added to the construct. An example of a suitable termination signal is the nopalin synthase gene termination sequence of *Agrobacterium tumefaciens* (Bevan, Nucl. Acids Res. 22, 8711–8921 (1984)).

In the in vivo method it is advantageous when the modified polysaccharides accumulate in harvestable organs, such as roots, leaves, stems, tubers, bulbs and seeds.

It is particularly surprising that it is possible according to the invention to produce fructans in plastids since it has been assumed heretofore that no sucrose or sucrose insufficient for this purpose would be present in plastids such as chloroplasts or amyloplasts. (Bird, I. F. et al., Phytochemistry 13, 59–64 (1974); Mares, D. J. et al., J. Exp. Bot. 29, 829–835 (1978)). In addition, in "Chloroplast metabolism, the structure and function of chloroplasts in green leaf cells" (Ed. Barry Halliwell, Clarendon Press, Oxford (1984) and in "Photosynthesis, molecular, physiological and environmental processes ($2^{nd}$ edition) (Ed. D. W. Lawlor) Longman Scientific & Technical, Essex, UK (1993) it is demonstrated that sucrose does not diffuse through the chloroplast membrane. The skilled person would therefore expect that fructan production in plastids is not possible. Sucrose is in fact the most important fructosyl donor in vivo (Dedonder, Meth. Enzyme 8, 500–505 (1966), Edelman & Jefford, New Phytol. 67, 517–531 (1968)). Sucrose can, in the plastids, also serve as substrate for a glucosyl transferase.

It has further been found according to the invention that, in addition to the presence of an enzyme not present in the wildtype, the (growing) conditions can be of influence on the degree of modification of the polysaccharide. Genetically identical transgenic potato lines were cultivated in the summer and the winter, respectively. Of these, those cultivated in the winter were found to contain a higher fructan content than those cultivated in the summer. Analysis of the starch granules from the potatoes further showed that in the case of the winter potatoes the starch granules were comparatively smaller and moreover that the size distribution was much more uniform compared to both the wildtype and the summer potatoes. In addition, clear differences could be observed between starch from the transgenic plants and starch from wildtype plants grown under the same conditions. In this manner it becomes possible to influence the polysaccharide modification. The conditions will herein be chosen such that the desired type of influence eventually results. These desirable conditions will sometimes be suboptimal (winter) and sometimes more optimal (summer).

The extent and nature of the modification in transgenic plants by varying the growing conditions can therefore result in inter alia smaller granules with a changed morphology. The morphology of suspended granular starch has a great influence on the rheological properties, including the viscosity of the gel during gelatinisation (so-called top viscosity). In addition, very small starch granules or particles with a size in the order of 1 micron are stable in aqueous solutions, which gives a non-precipitating suspension (latex). This is advantageous in the final gelatinisation step, but also in the pumping and storage of starch suspensions in industrial applications. As a result of the relatively large surface/volume ratio specific applications such as biologically degradable slow-release matrix can also be developed. Considerable interest in these so-called small starch particles can be discerned in the literature in recent years. Relatively small starch granules are occasionally found in nature in exotic plants. However, this type of small starch granules is difficult to extract and moreover does not have the desired properties which potato starch possesses.

The invention therefore further relates to a population of modified starch granules which have a smaller diameter and more uniform granule size distribution compared to starch granules originating from a wildtype plant and which can be used in foodstuffs as fat substitute and to encapsulate aromatic substances and/or flavourings. They are also suitable for non-food applications such as for instance paper coatings, as separating material or column material for chromatography, as carrier material for catalysts, as carrier-material for pigment, as basis for cosmetic creams, in paints, as slow release systems for agrochemicals and the like.

In gelled starch, i.e starch heated above the gelatinisation temperature in excess water (>70% (m/m)), starch pastes and other water-containing starch products such as bread and biscuits, retrogradation occurs after a few hours or days, this manifesting itself in the material becoming stiffer or brittle ("ageing"). The whole process of retrogradation includes the reforming of molecular structures in (partially) destructured systems, resulting in a change, usually seen as a deterioration, in the physical properties of the product. Examples of undesired changes are gels becoming unstable through crystallization, followed by separating out of water (syneresis), bread and biscuits becoming "stale" and biologically degradable plastics on a basis of starch becoming brittle. It is assumed in the literature that retrogradation can be inhibited or prevented either by substitution of the crystallizable chains in both amylose or amylopectin or by developing starches with fewer crystallizable components (amylose-free or "waxy" starches). The obtaining of derivatized or fructosylated starch, including fructosylated amylose and/or amylopectin would hereby seem very relevant for both the food and the non-food sectors.

By direct or indirect modification and/or by varying the conditions in which a transgenic plant grows the retrogradation behaviour of a polysaccharide such as starch can be changed according to the invention.

The invention thus further relates to the use of modified polysaccharides of which the retrogradation behaviour has been changed for the improvement of the shelf-life of bakery products such as biscuits and bread, or of sauces. Polysaccharides modified in this manner can further be used in non-food applications such as bioplastics, drilling liquids and glues.

In addition to the in vivo method according to the invention, the placing of the polysaccharide in contact with a sugar group-transferring enzyme, such as a fructosyl transferase or glucosyl transferase, can also be effected in vitro. In practice this entails an incubation of the substrate with the enzyme under suitable conditions in respect of temperature, pH, ionic strength and the like.

Before using these enzymes in vitro they are preferably first fully or partly purified. Natural or heterologous hosts can be used as source. The purification of fructosyl transferases from their natural host is for instance described for levan sucrase of *B. subtilis* by Ebskamp et al., Bio/techn. 12, 272–274 (1994). Other bacterial levan sucrases are for instance found in *Bacillus amyloliguefaciens* (Tang et al., Gene 96, 89–93 (1990)), *Streptococcus mutans* (Shiroza & Kurazitzu, J. Bacteriol. 170, 810–816 (1988)) and *Zymonas mobilis*.

The purification of sucrose sucrose fructosyl transferase (SST) from the onion is found in Angenent et al. on pages 173–184 of "Inulin and Inulin-containing crops", A. Fuchs (Ed.) Elsevier Science Publishers B.V. (1993) or in PCT/NL95/00241. Other fructosyl transferases from plants are for instance fructan fructan fructosyl transferase (FFT), sucrose fructan fructosyl transferase (SFT) and glucose fructan fructosyl transferase (GFT), which can for instance be isolated from onion, barley, wheat or Jerusalem artichoke.

When use is made of a heterologous host as source for the sugar group-transferring enzyme, this host will first have to be activated to production of the desired enzyme by transformation with a construct coding for the enzyme. The enzyme can subsequently be isolated from the host in per se known ways. An example of a suitable expression system for *E. coli* is the QIAexpress expression system (Qiagen Inc., USA).

In vitro modification of polysaccharides with a sugar group-transferring enzyme, whether or not purified, such as fructosyl or glucosyl transferase, can be performed in a manner known to the skilled person in a suitable buffer, containing in any case a fructose donor. The levan sucrase of *B. subtilis* functions well for instance in 50 mM phosphate buffer (pH 6.0) with 1% Triton, 100 $\mu$M PMSF and 20 mM sucrose. Fructosyl transferases can in determined conditions also transfer fructose to water in addition to the polysaccharide. Because this does not enhance the efficiency of the reaction, the reaction can also be performed in a low-water or water-free environment.

In both the in vivo and in vitro method natural as well as modified versions of the sugar group-transferring enzyme can be applied, while combinations of a plurality of enzymes of eukaryotic as well as prokaryotic origin can also be applied. By means of—genetic modification the properties such as substrate—affinity, activity and the like can also be influenced.

The transfructosylation or transglucosylation reaction can in principle be performed on any fructose or glucose acceptor, respectively. Recommended however are polysaccharides such as starch, cellulose, fructan, pectin, hemicellulose, amylose, amylopectin etc. Starch is usually built up of two types of glucane polymers, amylose and amylopectin. Amylose consists of substantially unbranched chains of $\alpha$1,4-linked glucose residues, while amylopectin, in addition to $\alpha$1,4-bonds, also has $\alpha$1,6-bonds which link chains mutually. In addition to starch, amylose and amylopectin can also be used separately as substrate for the modification.

The present invention will be further elucidated by means of the following examples, which are only given by way of illustration but are not intended to limit the invention in any way whatsoever.

EXAMPLES

Example 1

In vitro Transfructosylation of Amylose, Cellulose and Starch

1. In vitro Transfructosylation of Amylose

It was investigated whether the levan sucrase enzyme is capable of using amylose as fructosyl acceptor. Chosen for this experiment was the levan sucrase of *Bacillus subtilis* coded by the sacB gene (Steinmetz M. et al. Mol. Gen. Genet., 200:220–228 (1985)). This enzyme preferably uses sucrose and fructan as fructosyl acceptor but it can use many other compounds as fructosyl acceptor in the transfructosylation reaction (Dedonder R. Meth. Enzyme. 8,500–505 (1966).

The enzyme was purified according to the method of Ebskamp et al. (Bio/techn. 12,272–274 (1994)) and incubated with 50 mM phosphate buffer (pH 6.0), 1% triton, 100 $\mu$M PMSF, $^{14}$C sucrose (Amersham Int. plc, UK) and 50% acetone in the presence of 20 $\mu$l amylose resin (New England Biolabs inc.). During the incubation for 18 hours at 30° C., $^{14}$C labelled fructose units will be incorporated in fructan and covalently linked to amylose. So as to be able to distinguish between $^{14}$C labelled fructan which is covalently linked to the amylose resin and $^{14}$C fructan which is captured in the amylose resin, purified levan sucrase of *Bacillus subtilis* was likewise incubated with 50 mM phosphate buffer (pH 6.0), 1% triton, 100 $\mu$M PMSF, $^{14}$C sucrose and 50% acetone in the absence of 20 $\mu$l amylose resin. After incubation for 18 hours at 30° C. the amylose resin was added to the reaction mixture. Both tubes with amylose resin were then washed repeatedly with 100 volumes of water. Since bacterial fructan is water-soluble, non-covalently linked $^{14}$C-labelled fructose and fructan is therefore largely washed away while all the covalently linked $^{14}$C-labelled fructose and fructan will remain behind in the amylose resin pellet.

Determination of the activity of the amylose resin by scintillation count revealed that the activity of the resin which was incubated in the presence of fructosyl transferase was 35 times higher than the activity of the amylose resin which was added after the 18 hour incubation period at 30° C. of the levan sucrase enzyme (table 1). This demonstrates that the levan sucrase enzyme of *Bacillus subtilis* is indeed capable of using amylose as fructosyl acceptor in the transfructosylation reaction.

TABLE 1

| Incubation with fructosyl transferase | |
| --- | --- |
| | nmol fructose bound to amylose resin |
| with resin | 20 |
| without resin | 0.6 |

2. In vitro Transfructosylation of Starch and Cellulose

In similar manner it was investigated whether the levan sucrase enzyme is also capable of using insoluble corn starch or insoluble cellulose isolated from cotton as fructosyl acceptor in vitro.

The experiment was performed in the same manner as the experiment with amylose, with the difference that, instead of with amylose, the enzyme was incubated with either 10 mg insoluble corn starch (Sigma Chem. Co, St. Louis, Mo. 063178, USA) or 10 mg insoluble cellulose isolated from cotton (Bio-Rad, Richmond, Calif., USA).

Determination of the activity of the starch or the cellulose by scintillation count revealed that the activity of the material incubated in the presence of fructosyl transferase was respectively 8 and 19 times higher than the activity of the material added after the 18 hour incubation period at 30° C. of the levan sucrase enzyme (table 2), while TLC analysis revealed that the total fructan synthesis was constant in all reaction mixtures. This demonstrates that the levan sucrase enzyme of *Bacillus subtilis* is indeed capable of using starch and cellulose as fructosyl acceptor in the transfructosylation reaction.

TABLE 2

Incubation with starch and cellulose

| Incubation with fructosyl transferase | nmol fructose per mg fructosyl acceptor |
|---|---|
| with cellulose | 57 |
| without cellulose | 3 |
| with starch | 70 |
| without starch | 9 |

Example 2
In vitro Transglucosylation of Amylose

In the same manner as described in example 1, under 1., it was investigated whether the dextran sucrase of *Leuconostoc mesenteroides* (Kobayashi et al., Biophys. Acta 614, 46 (1980)) can transfer glucose of the glucose-donor sucrose to the glucose-acceptor amylose. Dextrans should then be formed.

The enzyme came from Sigma-Aldrich N.V./S.A. and was tested in reaction mixtures of 50 µl. Each reaction mixture contains 150 mM $^{14}C$ sucrose (Amersham Int. plc, UK), 15 mM NaAc (pH 5.2), 0.5 units of dextran sucrase, with or without 20 µl amylose resin. The whole was incubated overnight at 30° C. and treated further as stated in example 1.

Table 3 shows that in the presence of amylose resin 5 times as much radioactivity is incorporated. This means that the enzyme can use amylose as glucose-acceptor.

TABLE 3

| | nmol glucose bound to amylose resin |
|---|---|
| with resin | 13.0 |
| without resin | 2.6 |

Example 3
Expression of sacB in Plastids of Tobacco Plants
1. Selection of the Gene Ala Met (SEQ ID NO:7), Smeekens et al., Nuci. Acid. Res. 13:3179–3194 (1985)) was chosen and coupled in reading frame to the levan sucrase gene.

2. Construction of 35S-fd-sacB-NOS in the Binary Vector (pFD-LS)

Plasmid pSTU94 was constructed by cloning the 0.5 kb NcoI-BamHI fragment, which codes for the ferredoxin peptide of Silene pratensis from pETFD100 (Met Ala Ser Thr Leu Ser Thr Leu Ser Val Ser Ala Ser Leu Leu Pro Lys Gin Gin Pro Met Val Ala Ser Ser Leu Pro Thr Asn Met Gly Gin Ala Leu Phe Gly Leu Lys Ala Gly Ser Arg Gly Arg Val Thr Ala Met Ala Thr Tyr Lys Val Thr Leu lie Thr Ser Ala Ser (SEQ ID NO:8), Pilon et al., J. Biol. Chem. 270, 3882–3893 (1995)), in vector pMTL22 digested with NcoI and BglII. In order to clone the ferredoxin transit sequence for the sacB gene the 1.9 kb NcoI-XhoI fragment of the vector pSTU42 was isolated and cloned in the vector pSTU04 digested with Eco47III and XhoI after the NcoI restriction site was blunted with Mung bean nuclease, in order to provide pSTU113. To clone the 35S promoter for the fd-sacB-NOS construct the 2.1 kb NcoI-XhoI fragment from plasmid pSTU113 was cloned in vector pPA2 digested with NcoI and XhoI in order to produce pSTU176. Subsequently The 3.0 kb SmaI-XhoI 35S-fd-sacB-NOS construct was then cloned in the binary vector pVMJ5, resulting in pFD-LS (FIG. 1).

Plasmid pSTU94 was constructed by cloning the 0.5 kb NcoI-BamHI fragment, which codes for the ferredoxin peptide of *Silene pratensis* from pETFD100 (Pilon et al., J. Biol. Chem. 270, 3882–3893 (1995)), in vector pMTL22 digested with NcoI and BglII. In order to clone the ferredoxin transit sequence for the sacB gene the 1.9 kb NcoI-XhoI fragment of the vector pSTU42 was isolated and cloned in the vector pSTU94 digested with Eco47III and XhoI after the NcoI restriction site was blunted with Mung bean nuclease, in order to provide pSTU113. To clone the 35S promoter for the fd-sacB-NOS construct the 2.1 kb NcoI-XhoI fragment from plasmid pSTU113 was cloned in vector pPA2 digested with NcoI and XhoI in order to produce pSTU176. Subsequently The 3.0 kb SmaI-XhoI 35S-fd-sacB-NOS construct was then cloned in the binary vector pVMJ5, resulting in pFD-LS (FIG. 1).

The pFD-LS plasmid was transformed by means of electroporation (Mattanovich et al. Nulc. Acids Res. 17,6447 (1989)) in *Agrobacterium tumefaciens* strain LBA4404. The construct was introduced into *Nicotiana tabacum* var. Samson NN using the leaf disc transformation method (Horsch et al. Science 227, 1229–1232 (1985)). Regenerated plants, which are referred to as FD-LS plants, were selected for kanamycin resistance and cultured on MS medium (Murashige and Skoog Physiol. Plant. 15, 473–497 (1962)).

3. Analysis of Transgenic Tobacco Plants

FD-LS plants were cultured both in tissue culture and in the greenhouse. Leaf material of greenhouse plants was cut off and ground in an eppendorf tube. After centrifugation for 5 minutes at 16000 rpm 1 µl of the supernatant was spotted on TLC (Caims A. J. and Pollock C. J. New Phytol. 109, 399–405 (1988)). The TLC was developed three times in 85:15 acetone:water and subsequently treated with atomized urea as already described by Wise C. S. et al., Analytical Chemistry 27, 33–36 (1955). This method stains mainly fructose and fructose-containing polymers. While no fructan accumulation could be detected in the wildtype strain, the screening of the transformants with the use of this method showed an extensive accumulation of fructans in these plants in an excess of 10% of the dry weight (FIG. 2).

In order to determine whether the fructans which are present in transgenic plants were localized in the chloroplast, chloroplasts were isolated. Protoplasts were first isolated from tissue culture plants by incubating small pieces of leaf in K3 medium (Bagy, J L and Maliga, P. Z. Pflanzenphysiol. 78,453–455 (1976)) supplemented with 0.4 M sucrose, 1.2% cellulase and 0.4% macerozym (K3S). During the overnight incubation these—enzymes digested the plantcell wall. Intact protoplasts have the feature that they float on K3S medium when they are centrifuged for 10 minutes at 600 rpm (80 g). Isolated protoplasts were washed with W5 medium (Menczel et al. Theor. Appl. Genet. 59, 191–195 (1981) and precipitated by centrifuging for 5 minutes at 600 rpm. The protoplasts were resuspended in 2 ml isolation buffer (0.33 M Sorbitol, 50 mM Hepes/KOH pH 7.3, 1 mM $MgCl_2$, 1 mM $MnCl_2$, 2 mM EDTA and 0.1% BSA) and lysated by pressing the protoplasts through a small capillary. Intact chloroplasts which were present in this lysate were isolated by separation of the organelles on a continuous Percoll gradient (Bartlett, S. C., Grossman, A. R. and Chua, N-H in: Hallick, R. B. and Chua, N-H. (eds) Methods in Chl. Mol. Biol. Elsevier Biomed. Press Amst./New York/Oxford pp 1981–1091 (1982)). Intact chloroplasts isolated from the gradient were washed by centrifuging them through 40% Percoll solution. A part of the chloroplast isolate was subsequently used for chlorophyll determination (Arnon D I, Plant Phys. (Bethesda) 41,1–14 (1949)). Based on quantities of chlorophyll, fructans were isolated from equal quantities of chloroplasts and protoplasts by extracting them three times with water. TLC analysis (FIG. 2) showed that the sample containing the isolated chloroplasts has the same quantities of fructans as intact protoplasts based on the quantity of chlorophyll. This indicates that the ferredoxin levan sucrase enzyme is present and active in chloroplasts.

Example 4
Expression of sacB in Plastids of Potato Plants
1. Introduction

In the same manner as in Example 3 the same gene construct was introduced into the potato *Solanum tuberosum* (var. kardal). Regenerated plants are referred to as FD-LS-A plants. Of one of these strains a number of plants was grown in the winter, while a number of genetically identical plants were grown in the summer. These plants are designated below as FD-LS-A-W or 192-2, respectively FD-LS-A-Z or 192-3.

2. Fructan Accumulation

FD-LS-A potato plants were cultured both in tissue culture and in the greenhouse. Leaf material of greenhouse plants was cut off and treated in the same manner as the leaf of tobacco plants (see Example 3, under 3.). In wildtype potato plants no fructan accumulation can be demonstrated. In the transgenic FD-LS-A potato plants fructans accumulate in an excess of 5% of the dry weight (FIG. 3).

3. Analysis of Starch from Transgenic Potato Tubers

The fructan level of plants grown in the winter was 5% of the dry weight, while that of plants grown in the summer amounted to only 1%. It follows herefrom that growing conditions play an indirect part in the amount of fructan which accumulates.

In addition, starch granules were isolated by cutting the tubers of FD-LS-A-W, FD-LS-A-Z and wildtype potatoes into large pieces and then carefully breaking the cells by a few short pulses at low speed with a polytron in 50 ml isolation buffer (50 mM Tris-Hcl pH 7.4, 10 mM EDTA, 1 mM NaSulphite, 1 mM DTT). The homogenate was filtered through two layers of Miracloth (Cal-biochem-novabiochem Corp., La Jolla, Calif., 92039, USA). The whole was subsequently left to stand for 48 hours whereby the starch granules precipitated. Thereafter the supernatant of the FD-LS-A plants, in which the soluble fructans are situated, was pipetted off from the starch granules. The starch was successively washed with 50 ml isolation buffer, three times 50 ml water and 50 ml acetone and suspended in water to a concentration of 0.5 mg starch/$\mu$l water. After each washing step the starch granules were left to precipitate for 48 hours. Roughly 5 mg of the thus obtained starch granules was stored without further treatment for electron-microscopy, polarization-microscopy and fructan detection. The remaining part was conditioned at 58% relative air humidity and 20° C. to a constant moisture content. This material was used for the other analyses.

3.1. Association of Fructan to Starch

Using a fructan-specific antibody it was determined whether fructans are associated to the FD-LS-A-W starch. For this purpose the structure of the starch granule was partially broken by incubating 2 $\mu$l of the FD-LS-A-W starch for 1 hour at 75° C. in 20 mM NaOH and spotting this on a nitrocellulose filter. In order to be able to distinguish between fructan which is associated to the starch granule and fructan which only adheres to the starch, a 5% fructan solution was added to wildtype potato starch. This starch was subsequently washed in the above described manner. 2 $\mu$l of this washed starch was then also incubated for an hour at 75° C. in 20 mM NaOH and spotted on the nitrocellulose filter. As positive control 2 $\mu$l of a 5% fructan solution was spotted on the nitrocellulose filter. This filter was then incubated for 30 minutes at 120° C. to bind the sugars to the nitrocellulose. Thereafter the filter was incubated for 4 hours in 5% protifar (Nutricia) to block all remaining antibody binding sites. The filter was thereafter incubated for 18 hours at room temperature with a $\frac{1}{1000}$ dilution of the fructan-specific antibody ($I_gG_3$ J606 of Organon Technica Corp., (West Chester. Pa. USA). The filter was then washed 4 times for 15 minutes in TBST solution (0.15 M NaCl, 10 mM Tris-HCl , pH 8.0, 0.05% Tween 20) and incubated for 2 hours with a second antibody labelled with alkaline phosphatase. The filter was subsequently washed again 4 times for 15 minutes in TBST solution. In order to detect the enzyme alkaline phosphatase the blot was stained with the reagent nitroblue tetrazolium (NBT) and 5-bromo-4-chloro-3-indolyl-phosphate (BCIP) in alkaline phosphatase buffer (100 mM Tris-HCl (pH 9.5), 100 mM Nacl) (Promega Corp., Madison, USA). After staining of the blot the fructan in the starch granule can be demonstrated.

After staining it can be seen on the filter that the starch isolated from transgenic FD-LS plants reacts specifically with the fructan-specific antibody while no fructan can be detected in the wildtype starch granules (FIG. 4). This means that the soluble fructan does not adhere to the starch granule, but that in the starch isolated from the FD-LS plants the fructan is strongly associated to the starch granule, at least so strongly that it cannot be washed away.

Starch from FD-LS-A-W and wildtype potato plants was then incubated for one, two or three hours at 75° C. in 20 mM NaOH. Longer incubation time in 20 mM NaOH at 75° C. break the starch granules even further open and thus make them more accessible to the fructan-specific antibody. After the treatment with caustic soda both starch samples were baked on the nitrocellulose filter and treated as described above. It can be seen on the filter that longer incubation times amplify the fructan-specific signal (FIG. 5). This means that the fructan does not lie on the surface of the starch granule but is included in the starch granule.

3.2. Shape and Size of the Starch Granules

Using Scanning Electron Microscopy (SEM) analysis, the shape and size of the starch granules from the different sources were examined. For this purpose starch from the FD-LS-A-W, FD-LS-A-Z and wildtype plants were dried in air for about 24 hours and subsequently mounted on copper sample holders using double-sided adhesive tape. Prior to the analysis the samples were sputtered with gold under vacuum. Analysis of the samples shows that the wildtype starch is comparable in morphology to regular potato starch with oval-like to round smooth granules in the size of 5 to 60 micron. However, the starch from the FD-LS-A plant has a clearly differing morphology. In both samples the fraction of small granules (circa 1–10 micron) has increased in quantity relative to the quantity of small granules in wildtype starch. The lower limit in the size of the granules is also lower than for the wildtype starch (respectively 1 and 5 micron). The large starch granules (larger than 15 micron) from the FD-LS-A-Z plants are elongate in form with a length about three times greater than the width, while the small starch granules (1–10 micron) are round. In contrast to the other starches, the starch from the FD-LS-A-W plants has a rough surface, which varies from very rough with deep cavities to slightly etched (FIG. 6).

For analysis under a polarization microscope, several droplets of the starches in water were arranged on an object slide, mixed with glycerol and covered with a cover glass. The preparations were analysed on a Zeis Axioplan microscope at magnifications in the order of 50 to 400 times with crossed polaroids as well as with phase contrast. The preparations were examined visually for the presence of double-refracting structures in the granules (so-called Maltese crosses). It was found herewith that all starches consist of double-refracting granules, which indicates a spherulitic, concentrically grown structure of the granules (FIG. 7).

Of the material conditioned at 48% relative humidity and 20° C., diffractograms were recorded on a Philips PC-APD diffractometer in the symmetrical reflection mode. Diffractograms were recorded in the angular range of 4–40° C. (2 θ) with a step size of 0.05° C. (2 θ) and a speed of 1.5° C. (2 θ)/minute. The diffractometer is equipped with a copper anode ($\lambda_{\alpha 1,2}$ is 0.1542 nm) and an Anton Paar TTK temperature chamber. Detection took place with a proportional detector. It was found herewith that the crystal structure and the crystallinity of the FD-LS-A-Z samples do not differ from those of the wildtype starch. Both samples have a B-type crystalline organisation, which indicates that the chain length distribution of the amylopectin in the FD-LS-A-Z starch does not differ greatly from the wildtype starch (FIGS. 8A & 8B).

3.3. Amylose Content

As measure of the amylose content of the starch the lysolecithin-complexing capacity (LLC) was determined. This was done by accurately weighing 6 to 7 mg starch and mixing it with a solution of 38.5 mg L-α-lysophosphatidylcholine (L-α-lysolecithin type I from egg yolk; Sigma [9008-30-4]) in 418 mg demineralized water. The sample was carefully mixed and on a Perkin Elmer DSC7 equipped with an automatic sample exchanger and calibrated at 10° C./minute with Gallium ($T_{onset}$36.9° C. and $\Delta H$29.06 J/g)) the samples were heated from 20 to 170° C. At 170° C. cooling took place to 20° C. at 200° C. per minute and scanned to 150° C. From the enthalpy of the endotherm at about 109° C. (which indicates "melting" of complexes of L-α-lysolecithin and amylose) the LLC was determined as a measure for the amylose content after correction for the moisture content. The LLC was expressed in relation to the complexing capacity of amylose from potato starch. Table 4 shows that the LLC of FD-LS- Z-A starch is lower than that of the wildtype starch. The LLC of wildtype starch is virtually comparable to the LLC (20–24%) observed in regular potato starch.

TABLE 4

| Starch | ΔH (J/g dry substance) | LLC*% (relative to potato amylose) |
|---|---|---|
| wildtype | 5.1 (±0.6) | 24 (±3) |
| FD-LS-A-Z | 3.4 (±0.6) | 16 (±3) |

The low LLC of the FD-LS-A-Z starch points either to a significantly lower amylose content or to a slight branching of the amylose, whereby complexing is prevented and the amylose content appears to be lower. This shows in any case that the FD-LS-A-Z starch clearly differs from the wildtype starch.

Example 5

Modification of Starch by FD-LS-MBP

1. Selection of the Gene

Starch biosynthesis takes place in the chloroplast. In order to modify the starch by the action of fructosyl transferases the levan sucrase enzyme was chosen which is coded by the sacB gene of *Bacillus subtilis* (Chambert et al. Biochimica et Biophisica Acta 1132, 145–153 (1992)).

In addition to the ferredoxin targeting signal of *Silene pratensis*, (Smeekens et al., Nucl. Acid Res. 13:3179–3194 (1985)) to target the levan sucrase to the plastids, the affinity of the levan sucrase for the glucose polymer was increased by including in the construct the gene which codes for the maltose binding protein (malE-gene) (Duplay et al. J. Biol. Chem. 259, 10606–10613 (1984)) of *E. coli*.

2. Construction of 35S-fd-sacB-malE-NOS in the Binary Vector (pFD-LS-MBP)

To make the 35S-fd-sacB-malE-NOS construct a 1110 bp NruI-BamHI fragment which codes for the maltose binding protein was generated by means of PCR. The primers which were used to amplify the fragment were 1: 5' GGGGGTCGCGAAAATCGAAG 3' (SEQ ID NO:1); and

2: 5' CCCCGGATCCGAATTATCAAATCC 3' (SEQ ID NO:2);

The NruI and BamHI restriction sites (in bold print) are present in the primers 1 and 2, respectively, and were used to clone the fragment in the plasmid pSTU176 digested with EcoR5 and BamHI. The 4.1 kb XbaI-XhoI fragment was subsequently cloned in pVMJ5 digested with XbaI-XhoI to make pFD-LS-MBP (FIG. 1). This plasmid was then transformed in *Agrobacterium tumefaciens* strain LBA4404 and introduced into *Nicotiana tabacum* var. Samson NN as described in example 2. Regenerated plants were named FD-LS-MBP plants.

3. Analysis of Transgenic FD-LS-MBP Plants

Screening of the transgenic FD-LS-MBP plants for fructan accumulation as described in example 2 revealed that fructans can be detected in these plants. In order to determine whether these plants likewise contain fructose in their starch granules, leaves of greenhouse plants were used for starch granule isolation. To isolate the starch granules the leaves were carefully broken by a few short pulses at low speed with a Polytron in isolation buffer (0.33 M Sorbitol, 50 mM Hepes/KOH pH 7.3, 1 mM $MgCl_2$, 1 mM $MnCl_2$, 2 mM EDTA and 0.1% BSA). The homogenate was filtered through 2 layers of Miracloth (Calbiochem-Novabiochem Corp. La Jolla, Calif., 92039 USA) and centrifuged at 4000×g for 10 minutes. The crude extract was resuspended in a few milliliters of isolation buffer and starch granules were isolated by sedimentation in a 100% Percoll solution. The starch granules were washed with water. They were then hydrolyzed with $H_2SO_4$ and the glucose and fructose content was determined by HPLC. Starch granules of wildtype tobacco plants contain no fructose but in purified starch granules of the FD-LS-MBP plants significant fructose levels could be detected. This demonstrates that the levan sucrase enzyme is capable of transfructosylating starch in vivo or that fructan molecules are taken up in the starch granules.

Example 6

Production of Modified Starch in Transgenic Crops

1. Selection of the Genes and the Plant Species

In order to test whether starch can also be modified in transgenic crops, such as potato, corn or wheat, *Solanum tuberosum* var. Kardal and *Zea mays* were selected. In order to modify starch in plants of these crops through the action of fructosyl transferases the levan sucrase enzyme was chosen which is coded by the sacB gene of *Bacillus subtilis* (Chambert et al. Biochimica et Biophisica Acta 1132, 145–153 (1992)). For tuber-specific expression in the potato a strong tuber-specific promoter, the sporamin promoter of *Ipomoea batatas*, was used. For a strong expression in the endosperm of corn the zein promoter of *Zea mays* (Wandelt et al., Nucl. Acids Res. 17, 2354 (1989)) was chosen.

The ferredoxin targeting signal from *Silene pratensis* (Smeekens et al., Nucl. Acid Res. 13:3179–3194 (1985) was once again chosen to direct the levan sucrase to the plastids. To increase the affinity of the levan sucrase for the glucose polymer the maltose binding protein of *E. coli* coded by the malE-gene (Duplay et al., J. Biol. Chem. 259, 10606–10613 (1984)) was also used here.

2. Construction of the Gene Constructs

Plasmids pSP-FD-LS and pSP-FD-LS-MBP (FIG. 1) were constructed by replacing a 0.8 kb EcoRI-NcoI fragment with the 35S promoter of respectively pFD-LS and pFD-LS-MBP by a 1.0 kb EcoRI-BspHI fragment of pIMO23 (Hattori et al., Plant Mol. Biol. 5,313–320 (1985)), which contains the sporamin promoter of *Ipomoea batatas*. The 1.0 kb EcoRI-BspHI fragment with the sporamin promoter was generated by PCR amplification. The primers which were used for the amplification are:

```
1: 5' GGCTGCAGGAATTCGATATCAAGC 3' (SEQ ID NO:3);
and

2: 5' GTGAGGGCTTTCATGATGGCAGATGAGA 3'
(SEQ ID NO:4);
```

The restriction sites which were used to clone the fragment are designated with bold print.

Plasmids pSP-FD-LS and pSP-FD-LS-MBP were subsequently transformed in *Agrobacterium tumefaciens* strain LBA4404 and introduced into *Solanum tuberosum* var. Kardal as described (Visser, pp:1–9. Plant Tissue Culture Manual B5, K. Lindsey (Ed), Kluwer Acad. Publ. Dordrecht, Netherlands (1991)). The regenerated plants were named respectively SP-FD-LS and SP-FD-LS-MBP.

Plasmids pZE-FD-LS and pZE-FD-LS-MBP (FIG. 1) were constructed by replacing a 0.8 kb EcoRI-NcoI fragment with the 35S promoter of respectively pFD-LS and pFD-LS-MBP by a 2.0 kb EcoRI-BspHI fragment containing the zein promoter of *Zea mays*. The 2.0 kb EcoRI-BspHI fragment with the zein promoter was generated by PCR amplification. The primers which were used for the amplification are:

```
1: 5' GGCTGCAGGAATTCACTCAATCAT 3' (SEQ ID NO:5);
and

2: 5' ACCTTGGTAGTCATGATTGTTAGGTCGT 3'
(SEQ ID NO:6).
```

The restriction sites which were used to clone the fragment are designated with bold print.

Plasmids pZE-FD-LS and pZE-FD-LS-MBP were subsequently transformed in *Zea mays*, as described (Hill et al., Euphytica 85, 119–123 (1995)). The regenerated plants were named respectively ZE-FD-LS and ZE-FD-LS-MBP.

3. Starch Analysis of Transgenic Potato and Corn Plants

Screening of transgenic SP-FD-LS and ZE-FD-LS plants for fructan accumulation as described in example 2 revealed that fructans can be detected in these plants. In order to determine whether the SP-FD-LS-MBP and ZE-FD-LS-MBP plants likewise contain fructose in their starch granules, leaves of greenhouse plants were used for starch granule isolation as described in example 3. The starch granules were purified and hydrolyzed with $H_2SO_4$ and the glucose and fructose content was determined by HPLC. Although starch granules of wildtype plants never contain fructose, fructose could be detected in the starch granules of both the SP-FD-LS-MBP and the ZE-FD-LS-MBP plants. This demonstrates that also in cultivated crops, such as potato and corn, starch can be. modified in vivo either by covalent linking of the fructan molecules to the starch or by inclusion of fructans in the starch granule or indirectly by changing the physiological conditions.

BRIEF DESCRIPTION OF THE DRAWINGS

FIGS. 6a–6f show SEM recordings of the starches wildtype, 192-3 (=FD-LS-A-Z) and 192-2 (=FD-LS-A-W) a: wild type starch (300×), b: wild type starch (600×), c: 192-3 starch (300×), d: 192-3 starch (600×), e: 192-2 starch (300×), f: 192-2 starch (600×).

FIGS. 7a–7c show polarization microscopy recordings (20× enlarged) of wildtype starch (a), 192-3 starch (b) and 192-2 starch (c).

SEQUENCE LISTING

<160> NUMBER OF SEQ ID NOS: 8

Figure 1:
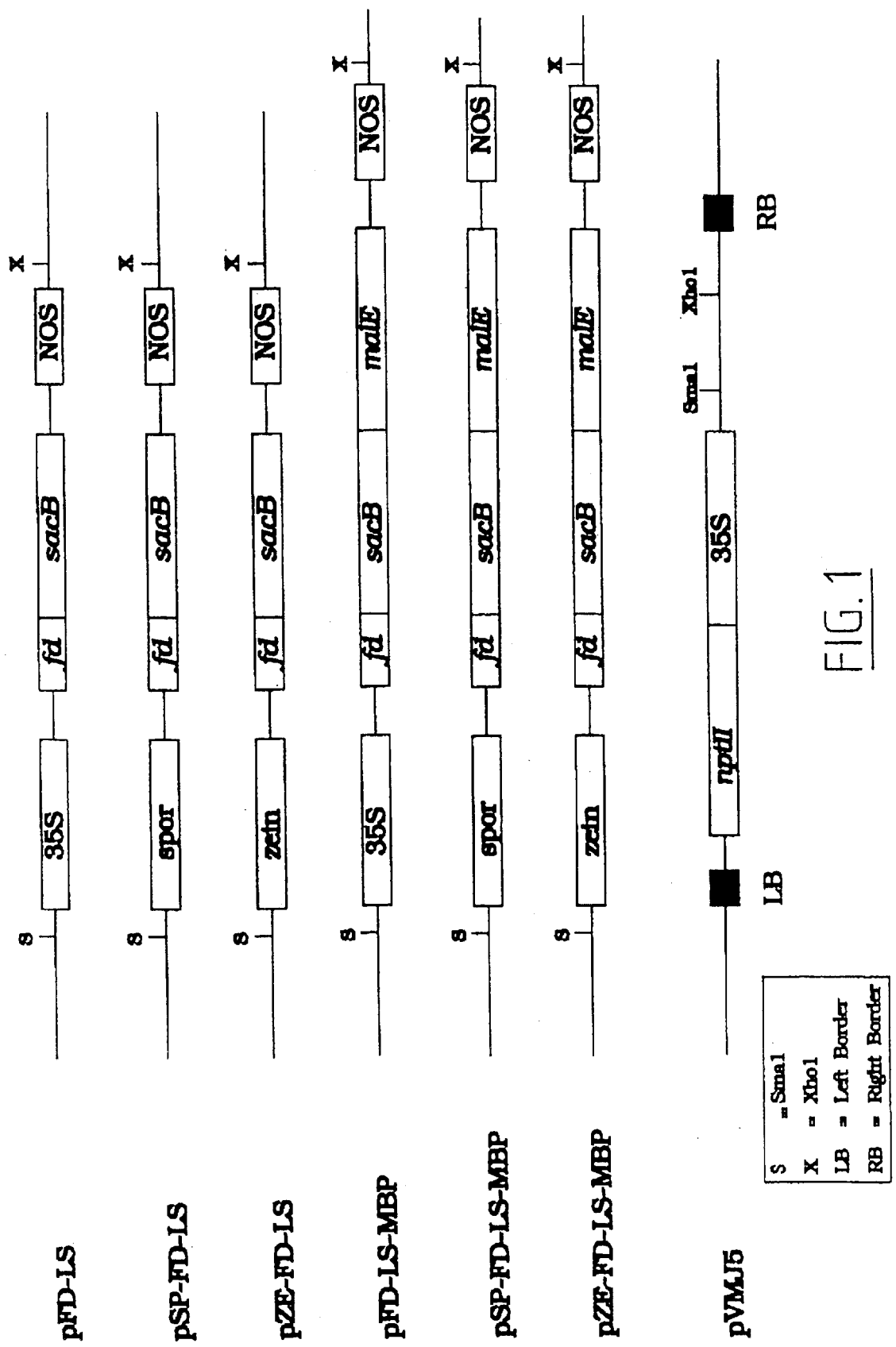
FIG. 1 is a schematic representation of the plasmids used.
Figure 2:
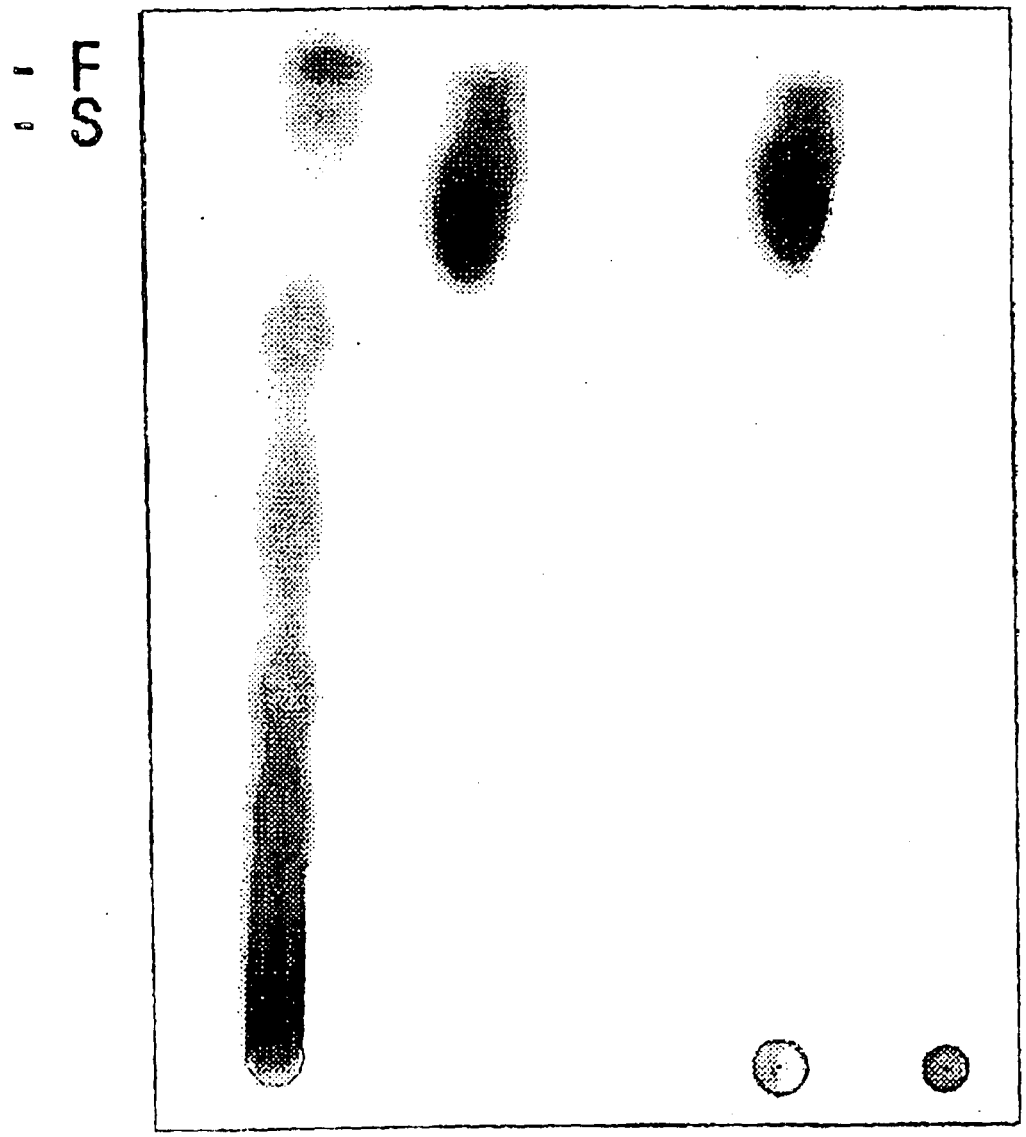
FIG. 2 shows a TLC analysis with fructans isolated from protoplasts (T) and purified chloroplasts (C) of wild-type tobacco plants (WT) and transgenic FD-LS plants (fd-ls) plants. Fructans were isolated from equal quantities of protoplasts and chloroplasts (based on the quantity of chlorophyll). Fructans which are larger than 20 fructose units remain behind on the application site. H=fructans isolated from *Helianthus tuberosus*; F=fructose; and S=sucrose.
Figure 3:
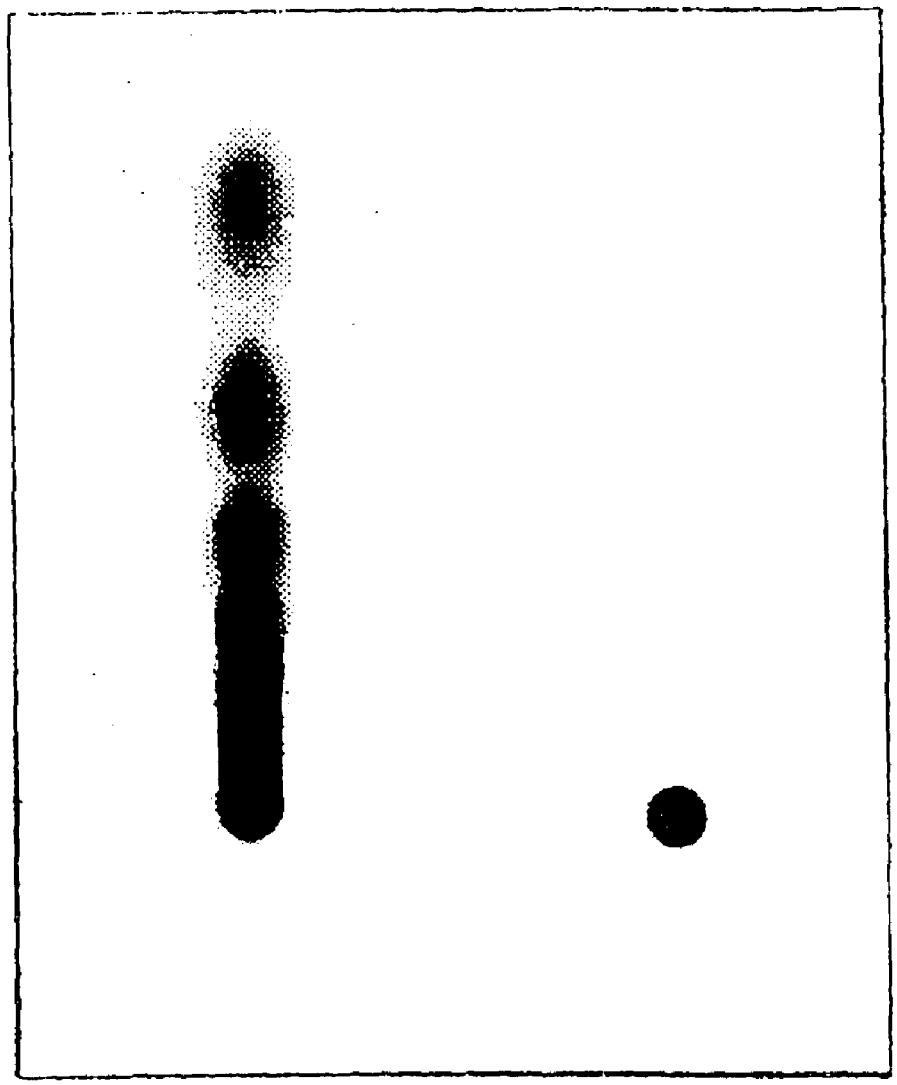
FIG. 3 shows a TLC analysis with fructans isolated from wildtype (WT) and transgenic FD-LS-A (fd-LS) potato plants. Fructans were isolated from equal quantities of leaf material. The fructans larger than 20 fructose units remain behind on the application site. M=fructans isolated from *Helianthus tuberosus*.
Figure 4:
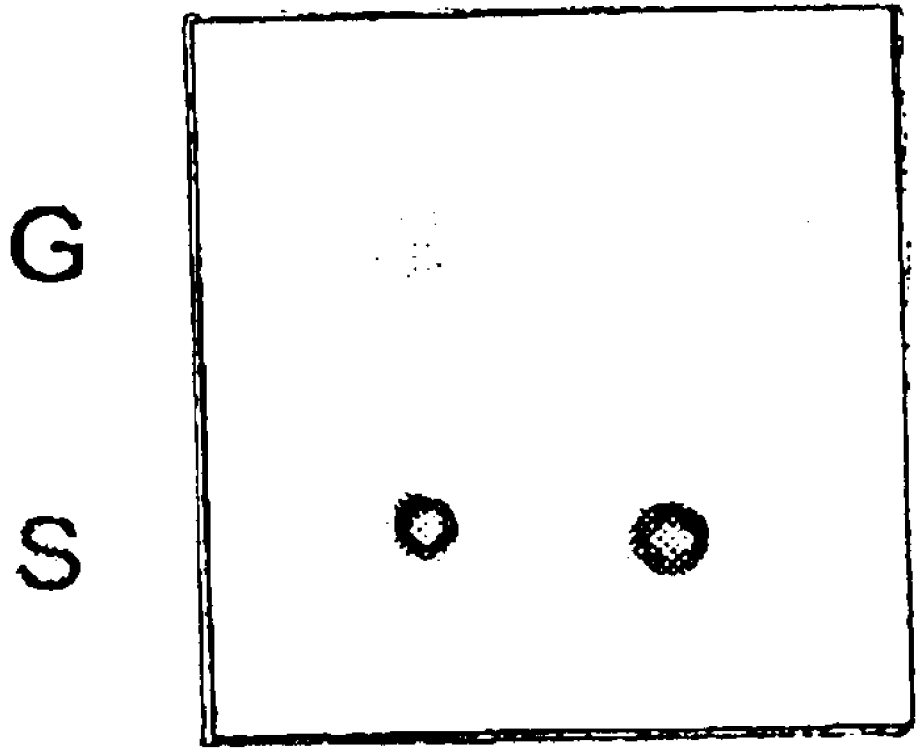
FIG. 4 shows the immunodetection of fructans in modified starch using a fructan-specific antibody. Starch granules were isolated from equal quantities of wildtype (C) and transgenic FD-LS-A-W (Fd-LS) potato tubers and prior to washing of the starch granules a 5% fructan solution was added to the wildtype starch. About 1 mg of the washed starch granules (G) was spotted on nitrocellulose next to 2 μl of a 5% fructan solution (S). Fructan present on the blot was made visible with a staining reaction.
Figure 5:
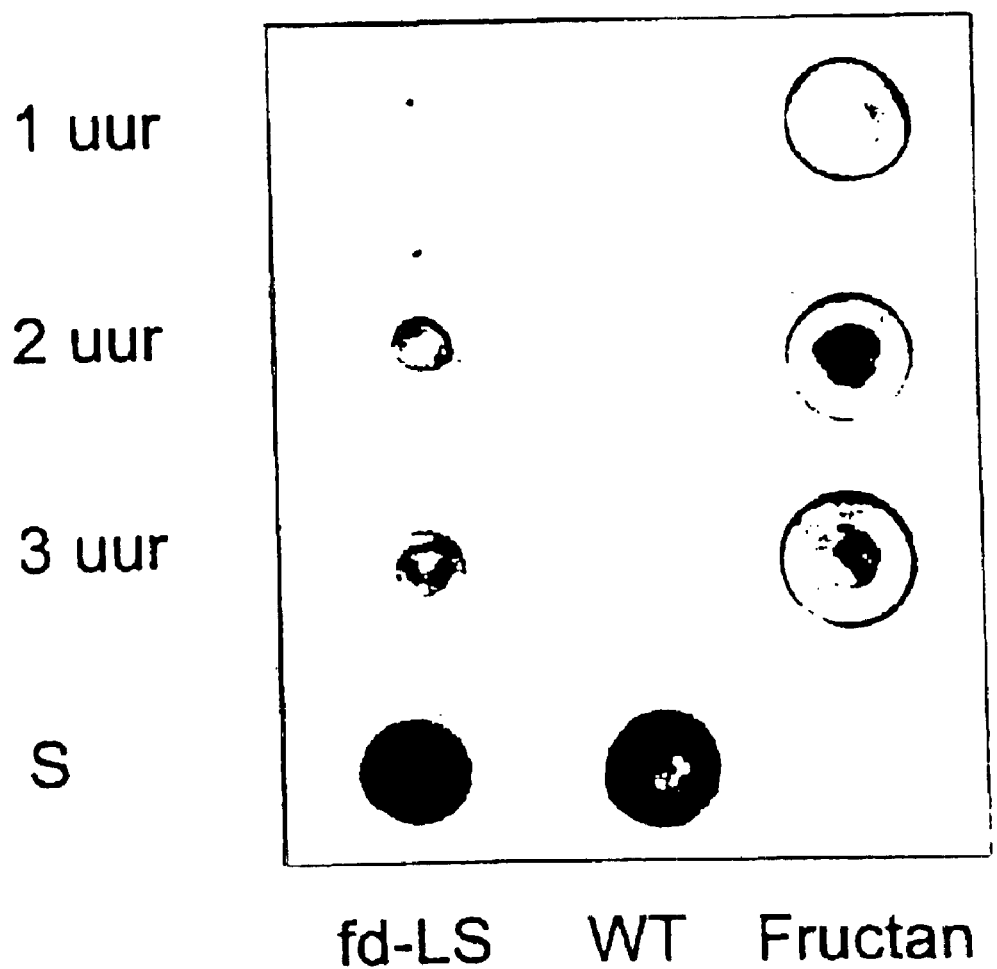
FIG. 5 shows the immunodetection of fructans in wildtype (WT) and transgenic FD-LS-A-W (fd-LS) starch granules. Isolated starch granules were incubated for 1, 2 or 3 hours in 20 mM NaOH at 75° C. to break open the starch granules. In order to assess whether the immunogenicity of the fructan changed under these conditions, 2 μl of a 5% fructan solution was incubated for 1, 2 or 3 hours in 20 mM NaOH at 75° C. After blotting on nitrocellulose the presence of the fructan was examined with a fructan-specific antibody. S is 2 μl of a 5% fructan solution.
Figure 8A:
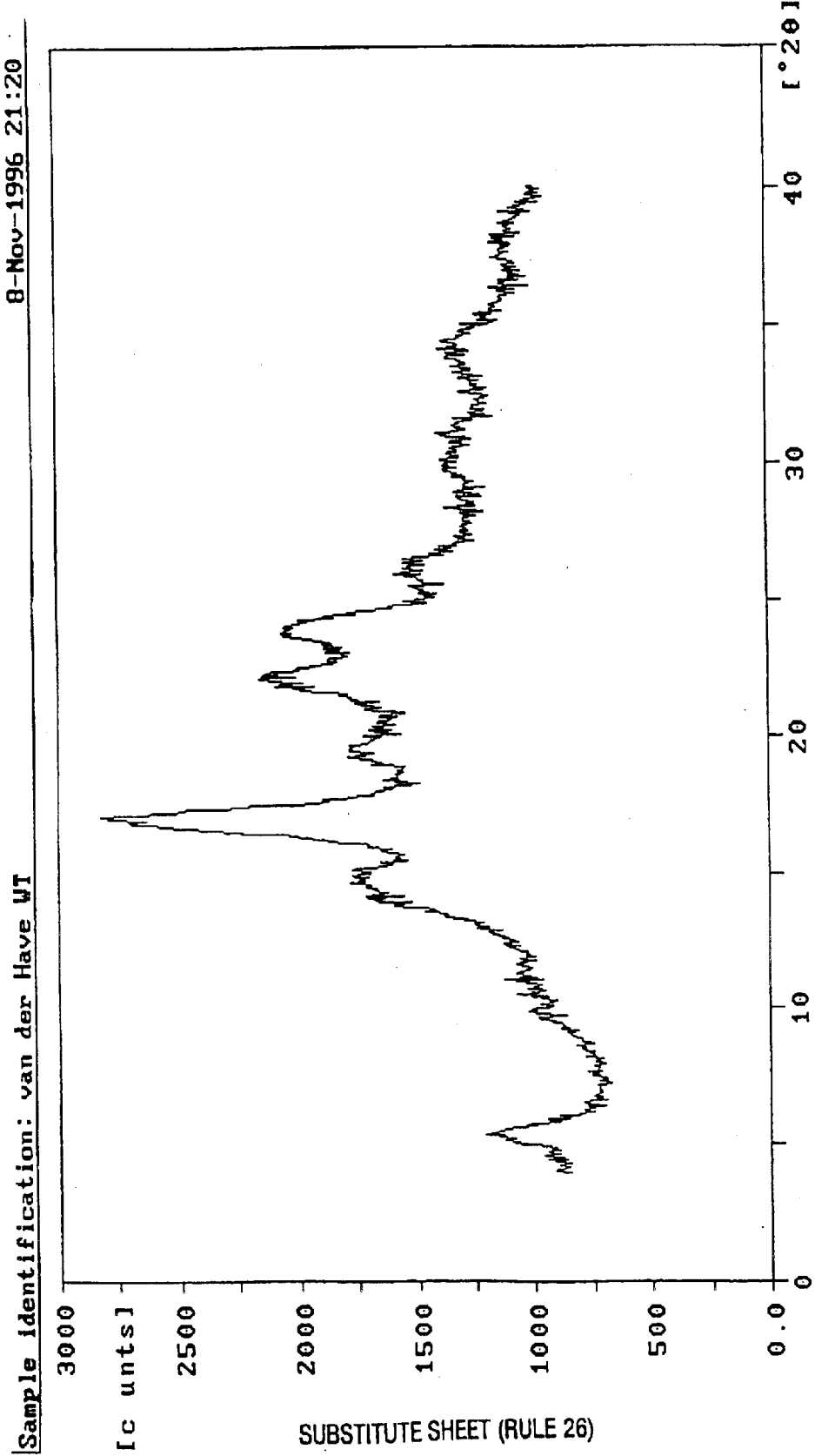
FIGS. 8a–8b show diffractograms of wt starch (a) and 192-3 starch (b).
Figure 8B:
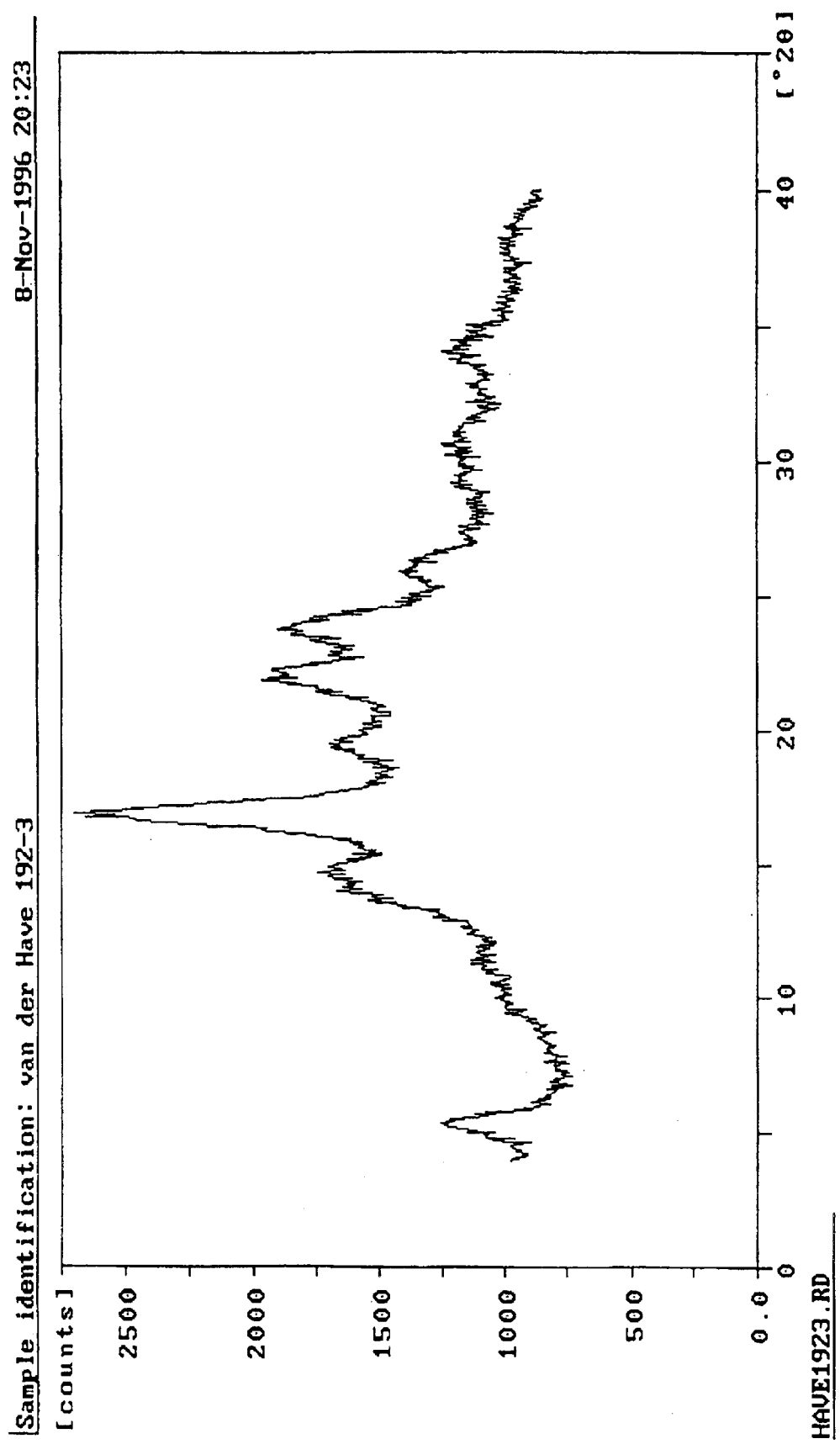

<210> SEQ ID NO 1
<211> LENGTH: 20
<212> TYPE: DNA
<213> ORGANISM: Artificial Sequence
<220> FEATURE:
<221> NAME/KEY: misc_feature
<223> OTHER INFORMATION: PCR Primer

<400> SEQUENCE: 1
gggggtcgcg aaaatcgaag                                              20

<210> SEQ ID NO 2
<211> LENGTH: 24
<212> TYPE: DNA
<213> ORGANISM: Artificial Sequence
<220> FEATURE:
<221> NAME/KEY: misc_feature
<223> OTHER INFORMATION: PCR Primer

<400> SEQUENCE: 2
ccccggatcc gaattatcaa atcc                                         24

<210> SEQ ID NO 3
<211> LENGTH: 24
<212> TYPE: DNA
<213> ORGANISM: Artificial Sequence
<220> FEATURE:
<221> NAME/KEY: misc_feature
<223> OTHER INFORMATION: PCR Primer

<400> SEQUENCE: 3
ggctgcagga attcgatatc aagc                                         24

<210> SEQ ID NO 4
<211> LENGTH: 28
<212> TYPE: DNA
<213> ORGANISM: Artificial Sequence
<220> FEATURE:
<221> NAME/KEY: misc_feature
<223> OTHER INFORMATION: PCR Primer

<400> SEQUENCE: 4
gtgagggctt tcatgatggc agatgaga                                     28

<210> SEQ ID NO 5
<211> LENGTH: 24
<212> TYPE: DNA
<213> ORGANISM: Artificial Sequence
<220> FEATURE:
<221> NAME/KEY: misc_feature
<223> OTHER INFORMATION: PCR Primer

<400> SEQUENCE: 5
ggctgcagga attcactcaa tcat                                         24

<210> SEQ ID NO 6
<211> LENGTH: 27
<212> TYPE: DNA
<213> ORGANISM: Artificial Sequence
<220> FEATURE:
<221> NAME/KEY: misc_feature
<223> OTHER INFORMATION: PCR Primer

<400> SEQUENCE: 6

```
accttggtag catgattgtt aggtcgt                                    27

<210> SEQ ID NO 7
<211> LENGTH: 48
<212> TYPE: PRT
<213> ORGANISM: Silene Pratensis

<400> SEQUENCE: 7

Met Ala Ser Thr Leu Ser Thr Leu Ser Val Ser Ala Ser Leu Leu Pro
1               5                   10                  15

Lys Gln Gln Pro Met Val Ala Ser Ser Leu Pro Thr Asn Met Gly Gln
                20                  25                  30

Ala Leu Phe Gly Leu Lys Ala Gly Ser Arg Gly Arg Val Thr Ala Met
            35                  40                  45

<210> SEQ ID NO 8
<211> LENGTH: 60
<212> TYPE: PRT
<213> ORGANISM: Silene Pratensis

<400> SEQUENCE: 8

Met Ala Ser Thr Leu Ser Thr Leu Ser Val Ser Ala Ser Leu Leu Pro
1               5                   10                  15

Lys Gln Gln Pro Met Val Ala Ser Ser Leu Pro Thr Asn Met Gly Gln
                20                  25                  30

Ala Leu Phe Gly Leu Lys Ala Gly Ser Arg Gly Arg Val Thr Ala Met
            35                  40                  45

Ala Thr Tyr Lys Val Thr Leu Ile Thr Ser Ala Ser
    50                  55                  60
```

What is claimed is:

1. Method for manufacturing modified polysaccharides, comprising placing a polysaccharide in contact with a sugar group donor and a sugar group-transferring enzyme in a transgenic plant cell, wherein the transgenic plant cell expresses a gene construct comprising at least one DNA sequence that codes for a sugar group-transferring enzyme selected from the group consisting of fructosyltransferases and glucosyltransferases, operably linked to a plastid-specific targeting signal sequence from the *Silene pratensis* ferredoxin gene.

2. Method as claimed in claim 1, wherein the transgenic plant cell is multiplied by regeneration to a plant tissue or complete plant or in cell suspension.

3. Method as claimed in claim 1, wherein the sugar group-transferring enzyme is a fructosyl transferase and the sugar group donor is a fructosyl donor.

4. Method as claimed in claim 1, wherein the sugar group-transferring enzyme is a glucosyl transferase and the sugar group donor is a glucosyl donor.

5. Method as claimed in claim 3, wherein the fructosyl transferase is selected from the group consisting of levan sucrase, sucrose sucrose fructosyl transferase (SST), fructan fructan fructosyl transferase (FFT), sucrose fructan fructosyl transferase (SFT) and glucose fructan fructosyl transferase (GFT), from plants or micro-organisms.

6. Method as claimed in claim 4, wherein the glucosyl transferase is selected from the group consisting of alternan sucrase, glucosyl transferase-I (GTF-I), glucosyl transferase-S (GTF-S), and glucosyl transferase-SI (GTF-SI) from micro-organisms.

7. Method as claimed in claim 2, wherein the transgenic plant, plant cell or plant tissue is cultured under conditions in which growth of the plant, plant cell or plant tissue is inhibited.

8. Transgenic plant or part thereof comprising at least one plant cell expressing a gene construct comprising at least one DNA sequence that codes for a sugar group-transferring enzyme selected from the group consisting of fructosyltransferases and glucosyltransferases, operably linked to a plastid-specific targeting signal sequence from the *Silene pratensis* ferredoxin gene.

9. Reproductive components of a plant as claimed in claim 8, selected from the group consisting of seeds, cuttings, tubers, bulbs, runners, and meristem, wherein each of the reproductive components comprises the gene construct.

10. The method as claimed in claim 1 further comprising the step of isolating modified polysaccharides from the transgenic plant cell.

* * * * *